United States Patent
Imagawa et al.

(10) Patent No.: US 10,893,840 B2
(45) Date of Patent: Jan. 19, 2021

(54) X-RAY DIAGNOSTIC APPARATUS

(71) Applicant: Toshiba Medical Systems Corporation, Otawara (JP)

(72) Inventors: Kazuo Imagawa, Nasushiobara (JP); Yoshiyasu Hayashi, Nasushiobara (JP); Masahiro Ozawa, Sakura (JP); Ko Fuchigami, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 238 days.

(21) Appl. No.: 15/802,658

(22) Filed: Nov. 3, 2017

(65) Prior Publication Data
US 2018/0125436 A1 May 10, 2018

(30) Foreign Application Priority Data
Nov. 8, 2016 (JP) .................. 2016-218027

(51) Int. Cl.
- *A61B 6/04* (2006.01)
- *A61B 6/00* (2006.01)
- *A61B 6/10* (2006.01)
- *A61K 49/04* (2006.01)
- *A61B 6/06* (2006.01)

(52) U.S. Cl.
CPC ............ *A61B 6/0407* (2013.01); *A61B 6/107* (2013.01); *A61B 6/4411* (2013.01); *A61B 6/4441* (2013.01); *A61B 6/547* (2013.01); *A61K 49/04* (2013.01); *A61B 6/06* (2013.01)

(58) Field of Classification Search
None
See application file for complete search history.

(56) References Cited

U.S. PATENT DOCUMENTS 3,720,817 A * 3/1973 Dinwiddie ............. A61B 6/102
600/1

FOREIGN PATENT DOCUMENTS

| JP | 2003-169795 | 6/2003 |
| JP | 2008-148866 | 7/2008 |
| JP | 2008-272290 | 11/2008 |
| JP | 2009-219552 | 10/2009 |
| JP | 2012-075773 A | 4/2012 |

* cited by examiner

*Primary Examiner* — Edwin C Gunberg
(74) *Attorney, Agent, or Firm* — Oblon, McClelland, Maier & Neustadt, L.L.P.

(57) ABSTRACT

According to one embodiment, an X-ray diagnostic apparatus includes a holding device and processing circuitry. The holding device movably holds an X-ray generator and an X-ray detector. The processing circuitry generates an X-ray image of the subject, based on an output of the X-ray detector. The processing circuitry sets an interference judgment region between the holding device and an interference object, based on a landmark in the X-ray image. The processing circuitry controls movement of the holding device, based on the set interference judgment region.

14 Claims, 18 Drawing Sheets

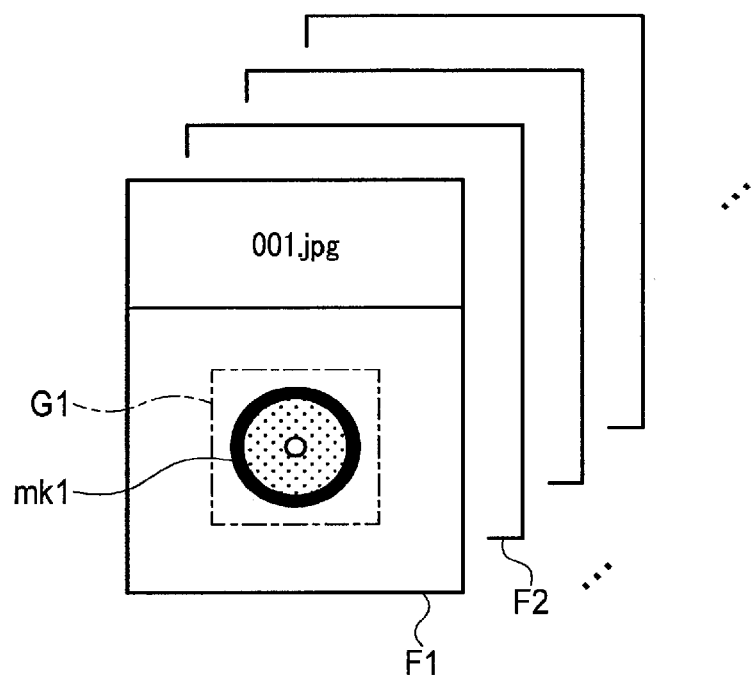
F I G. 4

| Image file name | Position of target | Size of target |
|---|---|---|
| 001.jpg | Position of landmark mk1 (Position of characteristic shape of magnetic pad) | Size of cube, $|x2+x3|$, $|y2+y3|$, $|zb|$, specified by $(x1+x2)\sim(x1-x3)$[mm] and $(y1+y2)\sim(y1-y3)$[mm] from position $(x1,y1)$ of landmark mk1, and by $(za-zb)$[mm] from height $(za)$ of bottom surface of couch top 91 |
| 002.jpg | Position of landmark mk2 (Position of bone of lower limb) | Size of semicylindrical shape specified by radius $r2$[mm] and length $y$[mm] from reference position deviating from position of landmark mk2 by predetermined position |
| .. | .. | .. |

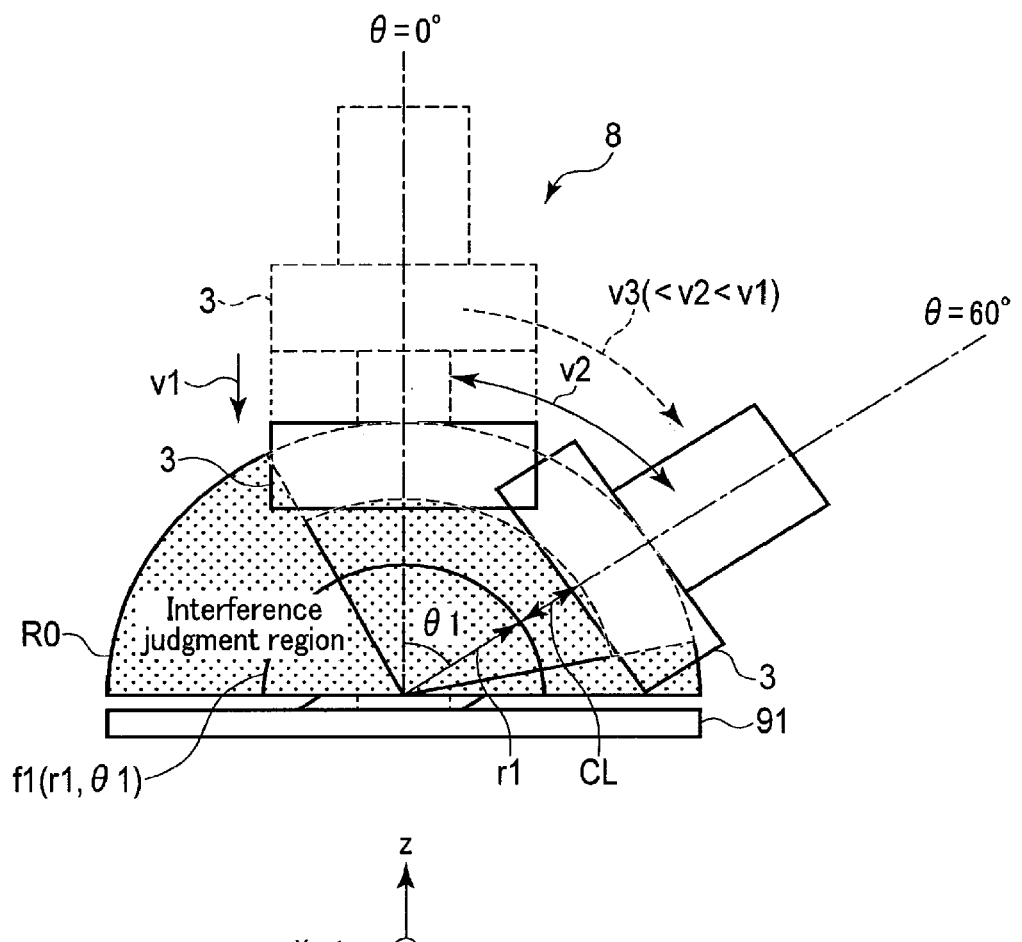
F I G. 15

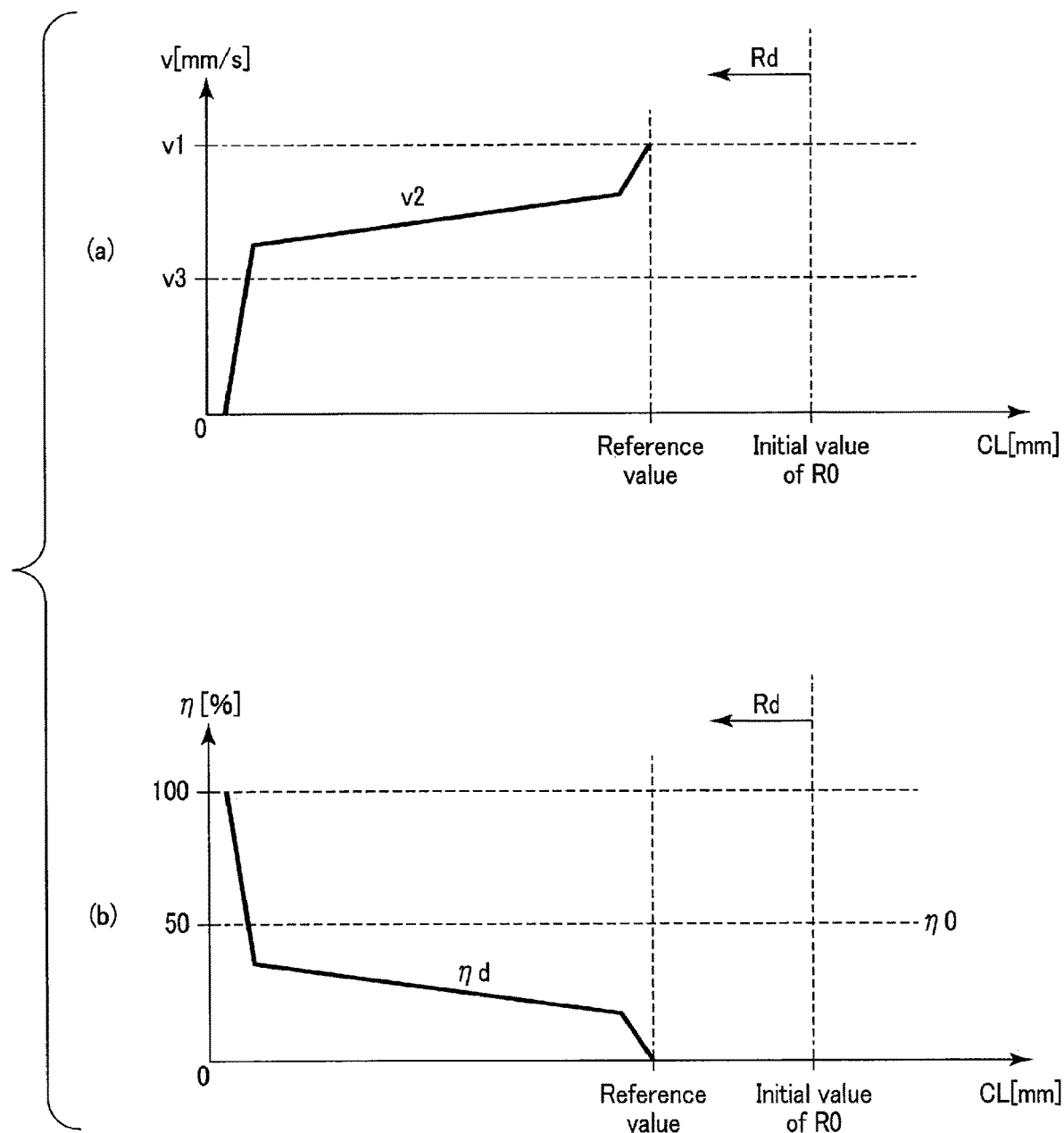
F I G. 16

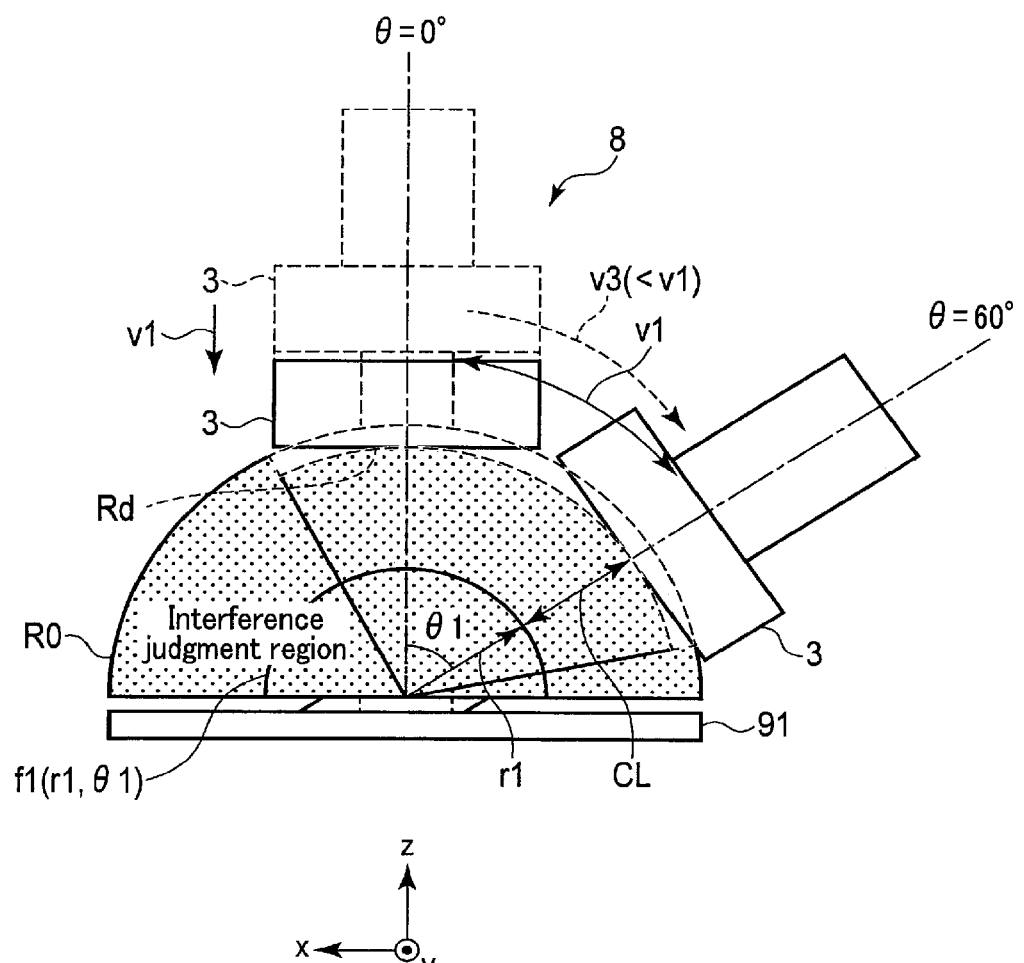
F I G. 17

X-RAY DIAGNOSTIC APPARATUS

CROSS-REFERENCE TO RELATED APPLICATIONS

This application is based upon and claims the benefit of priority from prior Japanese Patent Application No. 2016-218027, filed on Nov. 8, 2016, the entire contents of which are incorporated herein by reference.

Field

Embodiments described herein relate generally to an X-ray diagnostic apparatus.

Background

In general, in an X-ray diagnostic apparatus for a circulatory organ, when a therapy technique is performed on a subject placed on a couch top, the subject can be imaged from a desired angle by moving a C arm which supports an X-ray generator and an X-ray detector. In this kind of X-ray diagnostic apparatus, an interference prevention function is widely used which prevents, at a time of X-ray imaging, a contact between a moving body such as a C arm, and interference objects such as a subject and a couch.

In the interference prevention function for preventing interference with the couch or the like, use is made of a model representing a couch or the like, which is composed of a couch top and accessories, by a planar shape. At a time of X-ray imaging, a clearance (distance) between the moving body and the model is calculated. If the clearance has decreased to a threshold or less, the moving body is decelerated or stopped while an alarm sound is being produced.

In the interference prevention function for preventing interference with the subject, use is made of an average model which represents an interference object by a semicylindrical shape (vault shape). At a time of X-ray imaging, a clearance between the moving body and the model is calculated. If the clearance has decreased to a threshold or less, the moving body is decelerated or stopped while an alarm sound is being produced. Thereby, at a time of X-ray imaging, a contact between the moving body and interference object can be prevented, and safety can be secured.

Normally, no problem arises with the above-described interference prevention functions. However, according to the inventor's study, in a region where the moving body is decelerated or stopped, there is a possibility that while safety is secured, the clinical usefulness (user-friendliness) deteriorates.

For example, the conventional interference prevention functions are unable to recognize objects other than the couch and patient. Thus, from the standpoint of securing safety, the region where the moving body is decelerated or stopped is set to be wider than the actual region. Consequently, according to the conventional interference prevention functions, it appears that the moving body is unnecessarily decelerated or stopped. It is thus possible that users, such as a doctor, have an impression that the clinical usefulness is low.

The object is to enhance the clinical usefulness while maintaining safety, with respect to the interference prevention function.

BRIEF DESCRIPTION OF THE DRAWINGS

FIG. 4 is a schematic view for describing image files in the first embodiment.

FIG. 5 is a schematic view for describing a table in the first embodiment.

FIG. 15 is a schematic view for describing the operation in the fourth embodiment.

FIG. 16 is a schematic view for describing a movement speed and a deceleration ratio in the fourth embodiment.

FIG. 17 is a schematic view for describing the operation in the fourth embodiment.

DETAILED DESCRIPTION

In general, according to one embodiment, an X-ray diagnostic apparatus includes a holding device and processing circuitry.

The holding device includes an X-ray generator and an X-ray detector. The X-ray generator is configured to generate X-rays which are emitted to a subject placed on a couch top. The X-ray detector is configured to detect X-rays which have passed through the subject. The holding device is configured to movably hold the X-ray generator and the X-ray detector.

The processing circuitry is configured to generate an X-ray image of the subject, based on an output of the X-ray detector.

The processing circuitry is configured to set an interference judgment region between the holding device and an interference object, based on a landmark in the X-ray image.

The processing circuitry is configured to control movement of the holding device, based on the set interference judgment region.

Various embodiments will be described hereinafter with reference to the accompanying drawings. In the embodiments below, a description is given of an X-ray diagnostic apparatus for a circulatory organ, which includes as a holding unit a floor-disposition-type C arm having end portions to which an X-ray generator and an X-ray detector (imaging system) are mounted. However, the embodiments are not limited to this. For example, the holding unit may be a ceiling-suspension-type C arm or Ω arm. In addition, the X-ray diagnostic apparatus may be a general-purpose X-ray diagnostic apparatus which is adaptive to circulatory organ diagnosis and digestive organ diagnosis.

First Embodiment

Figure 1:
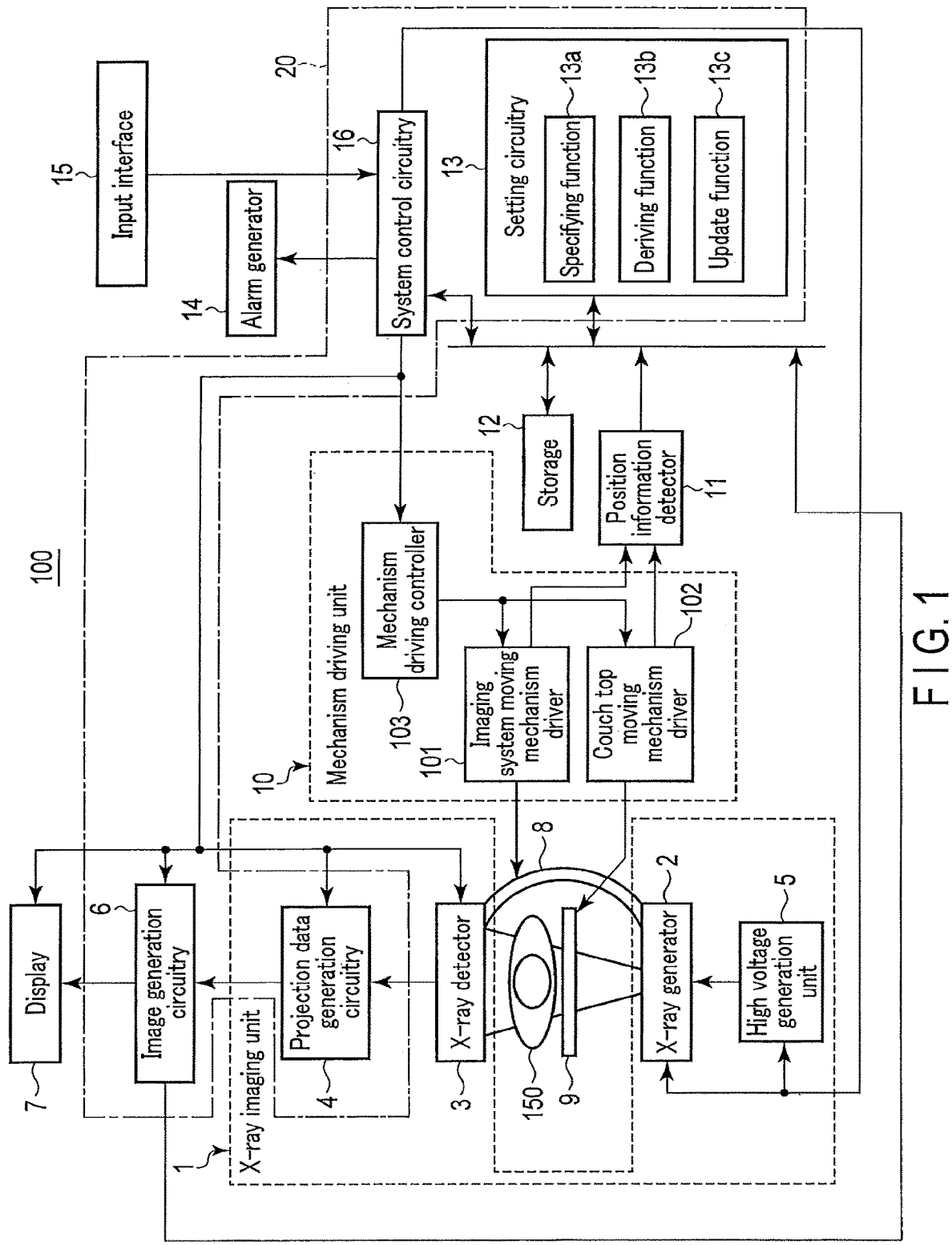
FIG. 1 is a schematic view illustrating the configuration of an X-ray diagnostic apparatus according to a first embodiment.

FIG. 1 is a schematic view illustrating the configuration of an X-ray diagnostic apparatus according to a first embodiment. An X-ray diagnostic apparatus 100 includes an X-ray imaging unit 1 which emits X-rays to a subject 150, detects X-rays which have passed through the subject 150, and generates projection data; image generation circuitry 6 which generates image data, based on the projection data; a display 7 which displays acquired image data; a holding device 8 including a holding unit which holds an X-ray generator 2 and an X-ray detector 3 (imaging system) of the X-ray imaging unit 1, and moves or rotates the X-ray generator 2 and X-ray detector 3 in a direction around the subject 150; and a couch unit 9 which moves a couch top, on which the subject 150 is placed, in a predetermined direction. The X-ray imaging unit 1 includes the X-ray generator 2, the X-ray detector 3, projection data generation circuitry 4, and a high voltage generation unit 5.

The X-ray diagnostic apparatus 100 further includes a mechanism driving unit 10 which supplies driving signals to various moving mechanism units (to be described later) which are provided in the holding device 8 and couch unit 9; a position information detector 11 which detects position information of the holding unit and an imaging system attached to this holding unit, and position information of the couch top provided in the couch unit 9; storage 12; setting circuitry 13 which judges a possibility of interference of the imaging system and holding unit with the subject 150, based on the position information of the imaging system and holding unit and the position information of the couch top; an alarm generator 14 which generates an alarm, based on a judgment result of the setting circuitry 13; an input interface 15 which executes an input of subject information, a setting of X-ray imaging conditions including an X-ray emission condition, and an input of various command signals; and system control circuitry 16 which comprehensively controls the above-described respective units and enables safe and efficient X-ray imaging for the subject 150. The projection data generation circuitry 4, the image generation circuitry 6, setting circuitry 13, and the system control circuitry 16 constitute processing circuitry 20 as hardware. The processing circuitry 20 may be a processor which calls and executes processing programs in the storage 12, thereby realizing the projection data generation circuitry 4, the image generation circuitry 6, the setting circuitry 13, and the system control circuitry 16 corresponding to the programs. Processing circuitry 20 may include the projection data generation circuitry 4, the image generation circuitry 6, setting circuitry 13, and the system control circuitry 16 as separated processors, and some of these processors may be integrated into one processors. Further, each of these processors may be divided into a plurality of processors. When the processing circuitry 20 includes a plurality of processors, each processor may be provided at physically distant position.

The X-ray imaging unit 1 includes a function of generating projection data, based on the amount of X-rays which have passed through the subject 150.

The X-ray generator 2 generates X-rays which are emitted to the subject 150 placed on the couch top 91. The X-ray generator 2 includes an X-ray tube and an X-ray collimator which forms an X-ray cone beam with respect to X-rays emitted from the X-ray tube. The X-ray tube is a vacuum tube which generates X-rays. The X-ray tube accelerates electrons, which are emitted from a cathode (filament), by a high voltage, and causes the electrons to collide with a tungsten anode, thereby generating X-rays. The X-ray collimator is located between the X-ray tube and the subject 150. The X-ray collimator narrows an X-ray beam, which is emitted from the X-ray tube, to a size of a predetermined emission field.

The X-ray detector 3 detects X-rays which have passed through the subject 150. As this X-ray detector 3, use can be made of an X-ray detector which directly converts X-rays to an electric charge, and an X-ray detector which first converts X-rays to light and then converts the light to an electric charge. Here, the former will be described, but the latter may be used. Specifically, the X-ray detector 3 according to this embodiment includes a planar detector which converts X-rays that have passed through the subject 150 to an electric charge and stores the electric charge, and a gate driver which generates driving pulses for reading out the electric charge stored in this planar detector.

The planar detector is configured such that minute detection elements are arranged two-dimensionally. Each of the detection elements includes a photoelectric film which senses X-rays and generates an electric charge in accordance with an incident X-ray amount; a charge storage capacitor which stores an electric charge generated in the photoelectric film; and a TFT (thin-film transistor) which reads out, at a predetermined timing, the electric charge stored in the charge storage capacitor (these constituent components are not shown). In addition, the stored charge is successively read out by the driving pulses which the gate driver supplies.

Next, the projection data generation circuitry 4 includes a charge/voltage converter configured to convert electric charges, which are read out in parallel in units of a row or a column from the planar detector, to a voltage; an A/D converter which converts an output of the charge/voltage converter to a digital signal; and a parallel/serial converter which converts the digitally converted parallel signals to a time-sequential serial signal.

The high voltage generation unit 5 includes a high voltage generator which generates a high voltage that is applied between the anode and cathode in order to accelerate thermions generated from the cathode of the X-ray tube; and an X-ray controller which controls X-ray emission conditions such as a tube current, a tube voltage, an emission time and an emission timing in the high voltage generator, in accordance with an instruction signal supplied from the system control circuitry 16.

The image generation circuitry 6 includes projection data storage and image arithmetic circuitry, which are not shown. The projection data storage successively stores time-sequential projection data supplied from the projection data generation circuitry 4 of the X-ray imaging unit 1, and generates two-dimensional projection data. On the other hand, the image arithmetic circuitry generates image data by executing an image process, such as a filtering process, on the two-dimensional projection data generated by the projection data storage. Moreover, the image arithmetic circuitry executes a compositing process and subtraction on the acquired plural image data.

The display 7 is composed of a display main body which displays a medical image or the like, internal circuitry which supplies a signal for display to the display main body, and peripheral circuitry such as a connector and a cable for connecting the display main body and the internal circuitry. The internal circuitry generates display data by superimposing additional information, such as subject information and projection data generation conditions, on the image data supplied from the image arithmetic circuitry of the image generation circuitry 6. The internal circuitry executes D/A conversion and TV format conversion on the acquired display data, and displays the resultant display data on the display main body.

On the other hand, the mechanism driving unit 10 includes an imaging system moving mechanism driver 101 which supplies driving signals to various moving mechanism units which are provided in the holding device 8 in order to move the imaging system in a desired direction; a couch top moving mechanism driver 102 which supplies a driving signal to a moving mechanism unit which is provided in the couch unit 9 in order to move the couch top 91, on which the subject 150 is placed, in a desired direction; and a mechanism driving controller 103 which controls the imaging system moving mechanism driver 101 and the couch top moving mechanism driver 102. In particular, the mechanism driving controller 103 includes a function of controlling the imaging system moving mechanism driver 101, based on an interference judgment result supplied from the setting circuitry 13 via the system control circuitry 16 with respect to the interference of the imaging system and holding unit with the subject 150, thereby decelerating the movement or rotation of the imaging system attached to the holding unit.

Figure 2:
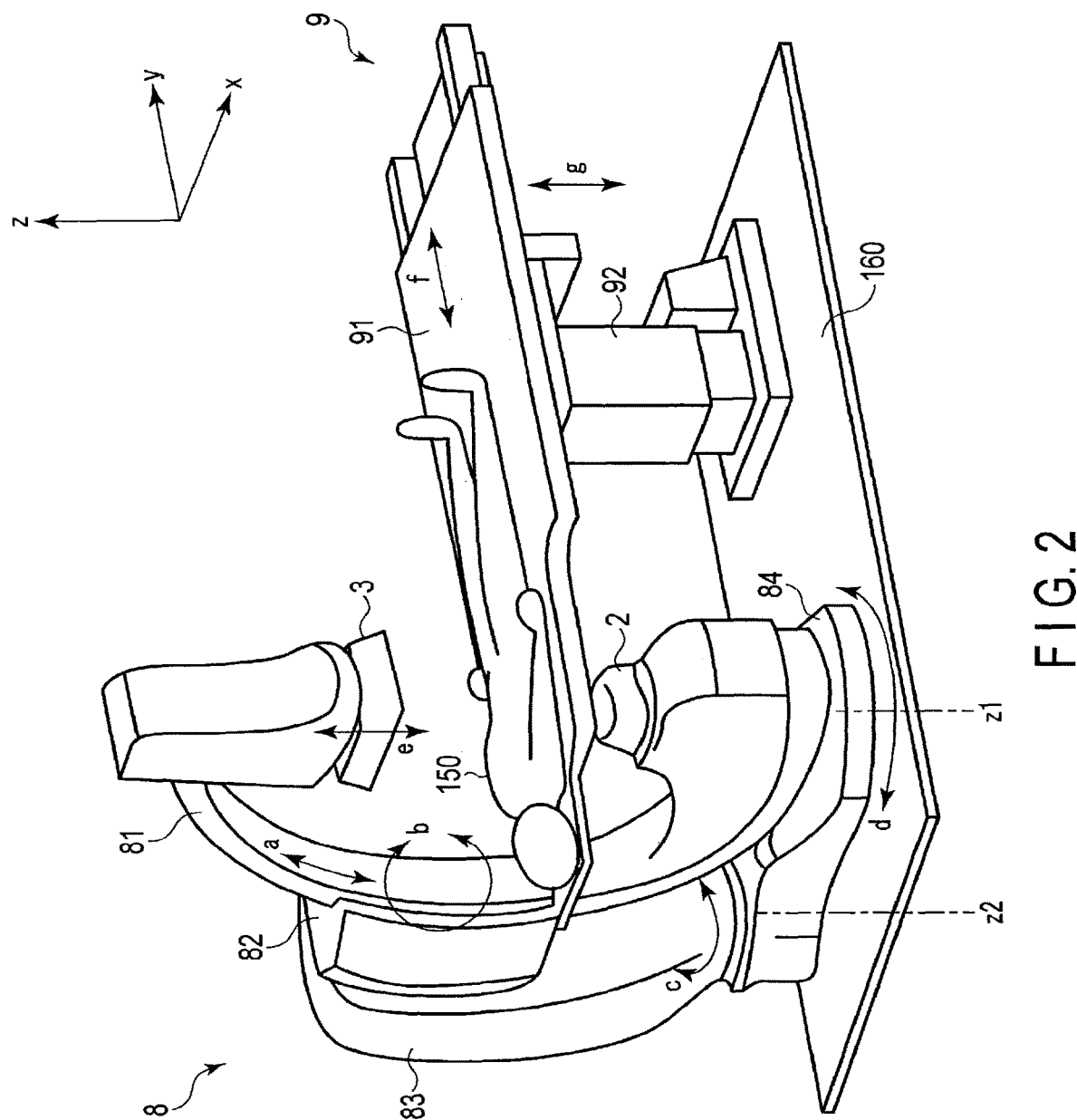
FIG. 2 is a perspective view illustrating the configuration of the X-ray diagnostic apparatus according to the first embodiment.

Next, referring to FIG. 2, a description will be given of the configurations of the holding device 8 and couch unit 9, and the movement or rotation of each of the units constituting the holding device 8 and couch unit 9. FIG. 2 illustrates the holding device 8 including as a holding unit 81 a C arm having end portions to which the X-ray generator 2 and X-ray detector 3 (imaging system) are attached; and the couch unit 9 including a couch top 91 on which the subject 150 is placed. In FIG. 2, for the purpose of simple description, the body axis direction of the subject 150 (i.e., the longitudinal direction of the couch top 91) is defined as a y axis. The center axis (rotational axis) direction of a stand 83 which holds the holding unit (C arm) 81 is defined as a z axis, and a direction perpendicular to the y axis and z axis is defined as an x axis.

Specifically, the X-ray generator 2 is attached to one end portion (lower end portion) of the holding unit 81, and the X-ray detector 3 is attached to the other end portion (upper end portion) of the holding unit 81, the X-ray generator 2 and X-ray detector 3 being opposed to each other. The holding unit 81 is held on a stand 83 via a holding unit holder 82. The holding unit 81 is attached to a side surface of the holding unit holder 82 in a manner to be slidable in a direction of arrow a. On the other hand, the holding unit holder 82 is attached to the stand 83 in a manner to be rotatable in a direction of arrow b, and the holding unit 81, too, rotates about the x axis in accordance with the rotation of the holding unit holder 82. In addition, the imaging system is attached to the end portions of the holding unit 81 in a manner to be slidable in a direction of arrow e. Besides, by the slide of the holding unit 81 in the a direction, the rotation of the holding unit holder 82 in the b direction and the slide of the imaging system in the e direction, the imaging system attached to the end portions of the holding unit 81 can be set at an arbitrary position and in an arbitrary direction relative to the subject 150 placed on the couch top 91.

On the other hand, one end portion of a floor turning arm 84, which is disposed on a floor surface 160, is attached in a manner to be rotatable about a rotational axis z1 (first rotational axis) relative to the floor surface 160. The stand 83 is attached to the other end portion of the floor turning arm 84 in a manner to be rotatable about a rotational axis z2 (second rotational axis). In this case, each of the rotational axis z1 of the floor turning arm 84 and the rotational axis z2 of the stand 83 is set in the z direction.

Specifically, the position information of the imaging system, which is attached to both end portions of the holding unit 81, is uniquely determined by the slide movement distance of the holding unit 81 relative to the holding unit holder 82, the rotational angle of the holding unit holder 82 in the b direction, the rotational angle of the floor turning arm 84 in the d direction, the rotational angle of the stand 83 in the c direction, and the slide movement distance of the imaging system relative to the holding unit 81.

Accordingly, the position information of the imaging system can be detected by detecting driving signals (e.g., by counting the number of driving pulses) which are supplied from the imaging system moving mechanism driver 101 of the mechanism driving unit 10 to various moving mechanism units of the holding device 8 (i.e., a holding unit sliding mechanism unit for sliding the holding unit 81, a holding unit holder rotating mechanism unit for rotating the holding unit holder 82 in the b direction, a stand rotating mechanism unit for rotating the stand 83 in the c direction, a floor turning arm rotating mechanism unit for rotating the floor turning arm 84 in the d direction, and an imaging system sliding mechanism unit for sliding the imaging system in the e direction) in order to move or rotate the holding unit 81, holding unit holder 82, stand 83 and floor turning arm 84 in predetermined directions.

Figure 3:
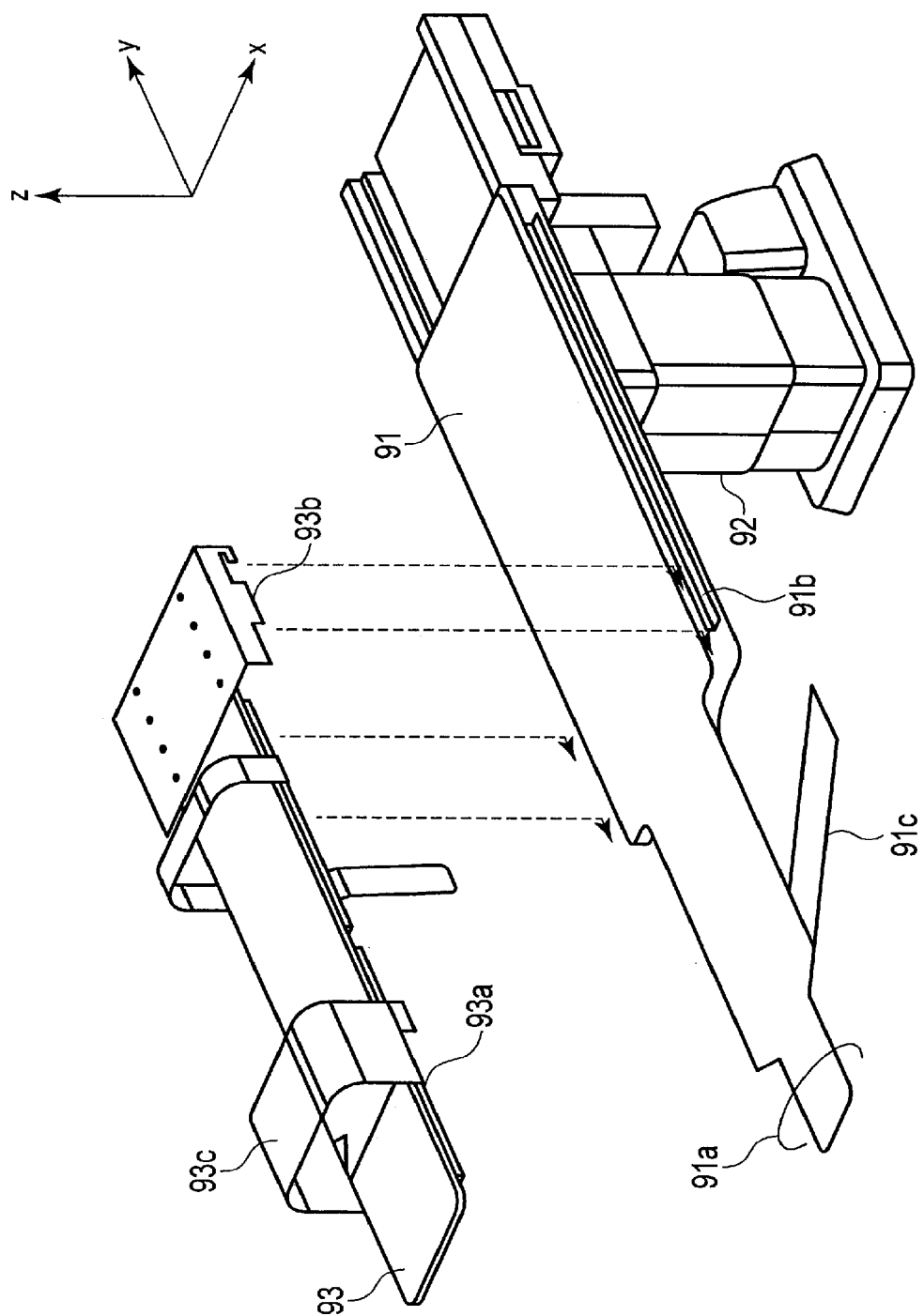
FIG. 3 is a perspective view for describing a CT auxiliary couch top in the first embodiment.

On the other hand, the couch 92 of the couch unit 9 is provided with a horizontal moving mechanism unit for horizontally moving the couch top 91, on which the subject 150 is placed, in the body axis direction (f direction), and a vertical moving mechanism unit for vertically moving the couch top 91 in a g direction. Here, the transverse width of the couch top 91 along the x axis varies in three steps of a leg side, a trunk side and a head side of the subject 150, and this transverse width decreases toward the head side. In addition, as illustrated in FIG. 3, an extension auxiliary couch top 93 for combination with CT (computed tomography), which extends the length of the head side, can be attached to the couch top 91. For example, a part 91a of the head side of the couch top 91 may be fitted between couch top displacement stoppers 93a on the back side of the extension auxiliary couch top 93, and attachment portions 93b provided on both side portions of the leg side of the extension auxiliary couch top 93 may be attached to attachment rails 91b which are provided on side portions of the leg side of the couch top 91. This extension auxiliary couch top 93 includes a guard 93c with a curved-surface frame shape 93c for protecting the subject. The extension auxiliary couch top 93 has a fixed transverse width along the x axis, and this transverse width is greater than the transverse width of the couch top 91. In addition, the couch top 91 may include an arm rest 91c on which an arm opened horizontally from the shoulder of the subject 150 is placed. The arm rest 91c has, for example, a substantially rectangular, planar shape. One short-side end portion of the arm rest 91c is horizontally rotatably provided on the couch top 91. This arm rest 91c is used, for example, when a contrast agent is injected in the arm of the subject 150. Instead of the arm rest 91c for the right arm shown in FIG. 3, an arm rest 91c for the left arm may be provided. Alternatively, respective arm rests 91c for the right arm and the left arm may be provided on the couch top 91.

Referring back to FIG. 1, the position information detector 11 detects the position information of the holding unit 81 and the imaging system attached to this holding unit 81, based on the driving signals supplied from the imaging system moving mechanism driver 101 of the mechanism driving unit 10 to the respective moving mechanism units of the holding device 8. The position information detector 11 also detects the position information of the couch top 91 provided in the couch unit 9, based on the driving signals supplied from the couch top moving mechanism driver 102 to the respective moving mechanism units of the couch unit 9.

The storage 12 includes memories such as an HDD (Hard Disk Drive), which store electric information, and peripheral circuitry such as a memory controller and a memory interface, which accompany these memories. The storage 12 stores programs which are executed by the system control circuitry 16 and setting circuitry 13, size information of the subject 150 (a semicylindrical model with a radius r1), size information of the imaging system and holding unit, and size information of the couch top 91. These pieces of size information are used in order to specify the position and size of an interference object, together with the position information of the imaging system and holding unit and the position information of the couch top 91. In addition, the storage 12 associates and stores the information of a landmark which is detectable from the X-ray image, and the position and size of a target corresponding to the information of the landmark. Here, the information of the landmark may be any information which can be detected from the X-ray image. For example, as the information of the landmark, an image for use in similarity judgment, or a characteristic amount for use in pattern recognition can be used as needed. In the present specification, a case in which the information of the landmark is an image will be described by way of example. Specifically, for example, as illustrated in FIG. 4 and FIG. 5, the storage 12 stores image files F1, F2, . . . , which include landmark images G1, and stores a table TB in which image file names for identifying the image files F1, F2, . . . , and positions and sizes of targets are associated and described. Aside from this, the storage 12 may store, with respect to each of landmarks, an image file including a landmark image and additional information indicative of the position and size of the target. In this case, too, there is no difference in the fact that the landmark image and the position and size of the target are associated and stored.

Here, as the landmark, for example, the following can be used as needed: (a) a magnetic pad of CARTO™, (b) an edge of the extension auxiliary couch top 93, (c) an edge of the arm rest 91c, (d) a head fixing instrument, (e) a phantom, (f) a bone of a lower limb of the subject 150, and (g) a bone of the head of the subject 150. In the case of (a) to (e), the landmark is the shape of a part of an instrument. In the case of (f) and (g), the landmark is the shape of a part of the subject 150.

Figure 6:
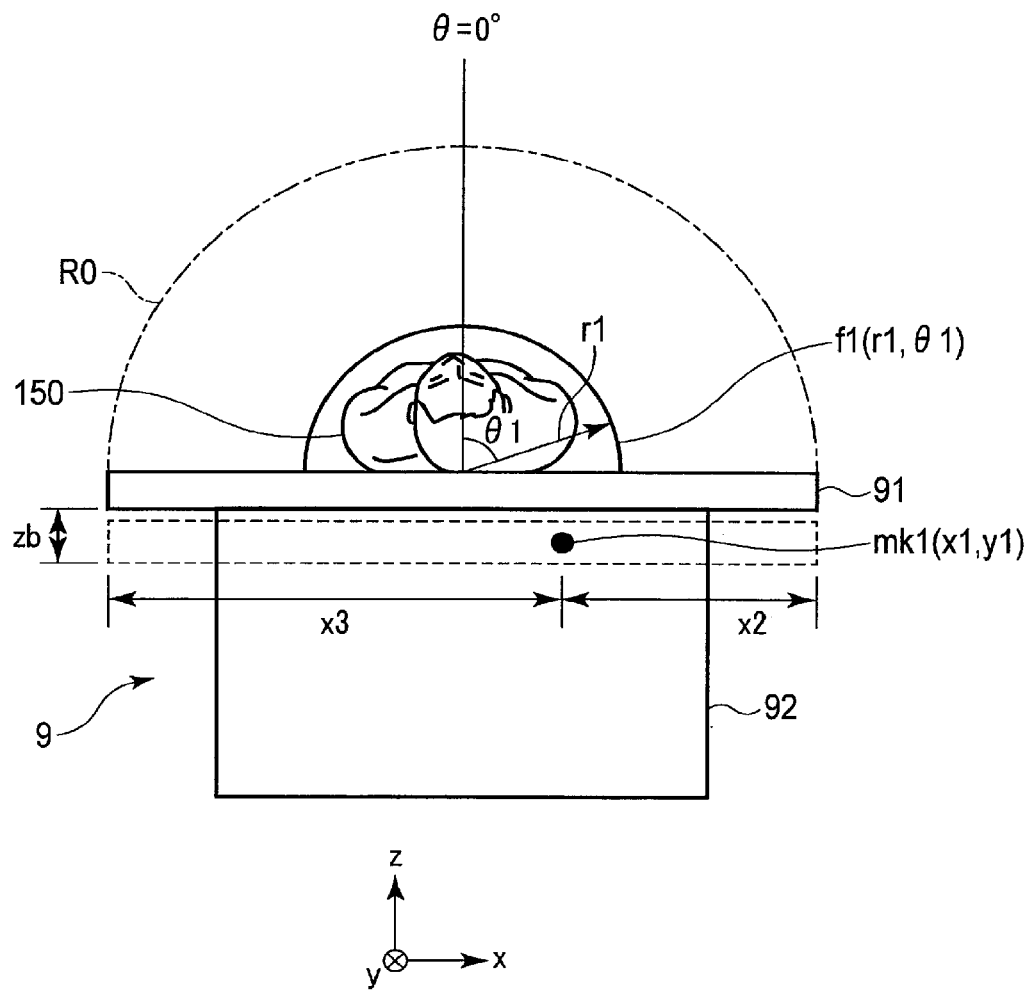
FIG. 6 is a schematic view for describing the position and size of an interference object in the first embodiment.
Figure 7:
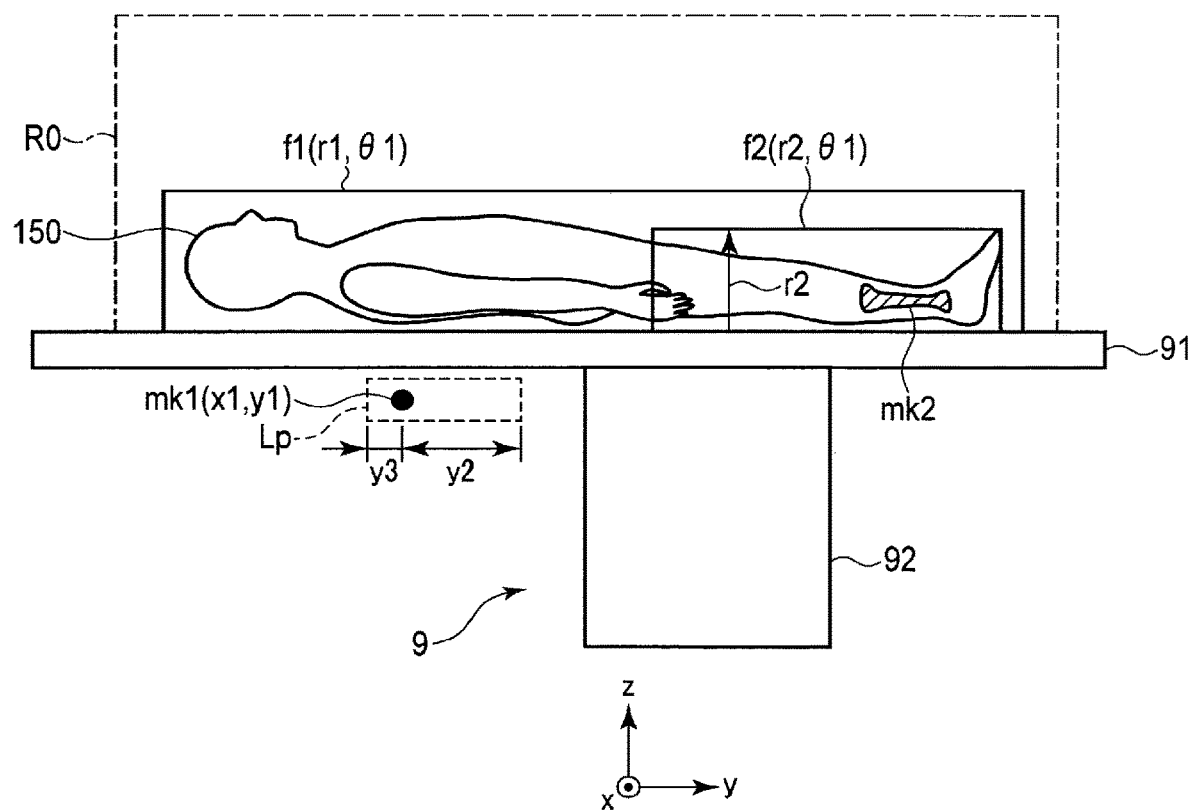
FIG. 7 is a schematic view for describing the position and size of the interference object in the first embodiment.

(a) To begin with, an example of the magnetic pad will be described. The landmark image G1 in the image file F1 is an X-ray image of a landmark mk1. The landmark mk1 is one of three magnetic pads which are used in a CARTO system which performs intracardiac mapping by utilizing magnetism in catheter ablation treatment. This magnetic pad is a device which generates magnetism for the mapping, and is disposed at a predetermined position of a device called "location pad". The magnetic pad of the landmark mk1 has a characteristic shape serving as a mark (landmark). As illustrated in FIG. 6 and FIG. 7, the magnetic pad is attached to the back side of the couch top 91 as a part of a location pad Lp. Besides, as illustrated in FIG. 5, FIG. 6 and FIG. 7, for example, the size of the location pad can be specified as a size of a substantial cube. The position of attachment of the location pad Lp slightly varies in the y axis direction of the couch top 91 at each time of attachment, but can be specified as the position of the landmark mk1 in the X-ray image. When the location pad Lp is attached to the back side of the couch top 91, the transverse width of an interference judgment region R0 is extended in accordance with the transverse width of the location pad Lp, even if the transverse width of the couch top 91 is narrow on the head side.

(b) Next, the edge of the extension auxiliary couch top 93 will be described. The extension auxiliary couch top 93 for a combination with CT is longer than the couch top 91 for angiography. In addition, unlike the couch top 91 having notches on the head side and trunk side, the entirety of the extension auxiliary couch top 93 is long in the transverse direction, and a collision will easily occur. As regards the extension auxiliary couch top 93, for example, the edge with the guard 93c is detected as the landmark. Thereby, the position and size of the extension auxiliary couch top 93 can be specified. Conventionally, the presence/absence of the extension auxiliary couch top 93 was set by the ON/OFF operation of a DIP switch. In the present embodiment, since the presence of the extension auxiliary couch top 93 can be detected based on the landmark in the X-ray image (the edge of the extension auxiliary couch top 93), this extension auxiliary couch top 93 can easily be used in real time. Besides, since the edge of the extension auxiliary couch top 93 can be used as the landmark, there is no need to add a landmark to the guard 93c or the like.

(c) Next, the arm rest 91c will be described. The arm rest 91c, which is provided on the couch top 91, projects from the couch top 91 in a horizontally oblique direction. Thus, the arm rest 91c easily collides with the holding device 8. Since this arm rest 91c has a predetermined characteristic shape, that is, an obliquely projecting, substantially rectangular shape, the arm rest 91c can easily be detected as the landmark. For example, by detecting an edge of the arm rest 91c as the landmark, the position and size of the arm rest 91c can be specified. In addition, since the landmark of the arm rest 91c can be detected from the X-ray image, this landmark can easily be used in real time. Moreover, for example, since the edge of the arm rest 91c can be used as the landmark, there is no need to newly add a landmark.

(d) Next, the head fixing instrument will be described. When the four corners of the head fixing instrument, as viewed from above, are used as landmarks, the position and size of the head fixing instrument can be specified even if the size of the head differs from subject 150 to subject 150. However, there is a case in which the four corners of the head fixing instrument do not serve as landmarks (a case in which the four corners do not have characteristic shapes). Thus, it is preferable that an instrument having landmarks at the four corners is used as the head fixing instrument.

(e) Next, the phantom will be described. The phantom is not used in a therapy technique by a doctor, but is used in calibration, etc. by a serviceman. An example of this kind of phantom is a helix phantom which is configured such that a plurality of steel balls for alignment are helically arranged on the surface thereof. When a part of the phantom is detected as a landmark, the interference control which involves deceleration and stop may be turned off, since the serviceman is performing calibration during this time and there is a low possibility that the X-ray detector 3 comes in contact with the phantom or couch top 91.

(f) Next, the bone of the lower limb will be described. The above-described (a) to (e) are optional instruments. This (f) is a part of the subject 150. The bone of the lower limb has a characteristic shape, and can be used as a landmark. Besides, as the landmark, either a shin bone or a calf bone of the bones of the lower limp can be used. In this example, the calf bone is used. The lower limb (leg) is thinner than the trunk. In general, as illustrated in FIG. 6 and FIG. 7, the size (f1 (r1, θ1)) of the subject 150 is specified by a model having a semicylindrical shape (vault shape) with a radius r1 (e.g., 30 cm) from the body axis center of the subject 150. By contrast, in the present embodiment, the size (f2 (r2, θ1)) of the vicinity of the lower limb is specified by a model having a semicylindrical shape with a radius r2 (e.g., 20 cm) from the body axis center of the subject 150, and the model with the radius r2 can be made smaller than the model with the radius r1.

(g) Next, the bone of the head of the subject 150 will be described. The bone of the head (hereinafter referred to as "skull") has a characteristic shape, and can be used as a landmark. For example, the skull includes a mandible having a U shape with an arrangement of teeth. When the mandible is detected as a landmark, the position and size of the skull can be specified from the X-ray image. Besides, the landmark is not limited to the mandible, and use can be made of a discretionarily chosen bone included in the skull, such as a frontal bone, a parietal bone, an occipital bone, a temporal bone, or a zygomatic bone.

When the skull is used as a landmark, even if the size of the skull is unknown, the size of the skull is specified from the 3D image of the head, and the size of the skull becomes known. Alternatively, even if the size of the skull is unknown, the size of the skull is specified from a CT image acquired in the past, and the size of the skull is known. In addition, the position of the skull can be specified based on the position of the landmark (e.g., mandible) in the X-ray image, and geometrical imaging conditions of the X-ray image. Accordingly, when the skull is used as a landmark, the landmark is detected from the X-ray image, and the position and size of the skull corresponding to the detected landmark can be specified.

A supplementary description is given. As the landmark, it is possible to use not only a model with a known size, but also a target with an unknown size. An example of the target with an unknown size is the above-described bone (skull) of the head. Aside from this, as the target with an unknown size, it is possible to use a discretionary target which is a part of the subject 150 and has a characteristic shape.

The setting circuitry 13 is a processor which calls and executes processing programs in the storage 12, thereby realizing a specifying function 13a, a deriving function 13b and an update function 13c corresponding to the programs. In the description of FIG. 1, the specifying function 13a, deriving function 13b and update function 13c are realized by the single setting circuitry 13. Alternatively, the setting circuitry may be composed by combining a plurality of independent processors, and the respective processors may execute the programs, thereby realizing the respective functions. Each of the specifying function 13a, deriving function 13b and update function 13c corresponds to a part of a setting function which sets an interference judgment region between the holding device 8 and an interference object, based on the landmark in the generated X-ray image. In other words, the setting function of the interference judgment region includes the specifying function 13a, deriving function 13b and update function 13c.

Here, the specifying function 13a is a function of detecting a landmark from an X-ray image, which was generated by the image generation circuitry 6, by referring to the information of the landmark in the storage 12, thereby specifying the position and size of the target corresponding to the detected landmark. For example, when the information of the landmark is an image, the specifying function 13a specifies the position and size of the target from the storage 12, based on the landmark image in the X-ray image generated by the image generation circuitry 6. In addition, for example, when the information of the landmark is a characteristic amount, the specifying function 13a extracts the characteristic amount from the X-ray image generated by the image generation circuitry 6, and specifies the position and size of the target from the storage 12, based on this characteristic amount.

The deriving function 13b is a function of deriving the position and size of an interference object including the target, couch top and subject, based on the specified position and size and the geometrical imaging conditions of the X-ray image.

The update function 13c is a function of setting (updating) the interference judgment region between the holding device 8, which includes the X-ray generator 2 and X-ray detector 3, and the interference object, based on the derived position and size. Here, to set the interference judgment region corresponds to each of a case of newly setting an interference judgment region and a case of updating an interference judgment region which was already set as a new one.

The alarm generator 14 includes, for example, a buzzer or a speaker (not shown). If it is detected in the system control circuitry 16 that the imaging system or holding unit 81 has reached the interference judgment region which is set around the subject 150, the alarm generator 14 generates an alarm sound, based on this detection result.

The input interface 15 is realized by a trackball for setting, for example, a region of interest (ROI), a switch button, a mouse, a keyboard, a touch pad for executing an input operation by a touch on an operation surface, a touch panel display in which a display screen and a touch pad are integrated, etc. The input interface 15 is connected to the system control circuitry 16. The input interface 15 converts an input operation, which was received from the operator, to an electric signal, and outputs the electric signal to the system control circuitry 16. In the present specification, the input interface 15 is not limited to an input interface including physical operational components such as a mouse and a keyboard. Examples of the input interface 15 include electric signal processing circuitry which receives an electric signal corresponding to an input operation from an external input device provided separately from the apparatus, and outputs this electric signal to the system control circuitry.

The system control circuitry 16 includes a processor and a memory, which are not shown. The above-described various pieces of information, which are input or set by the input interface 15, are stored in the memory. In addition, based on these input pieces of information and set information, the processor comprehensively controls the respective units of the X-ray diagnostic apparatus 100, and executes safe and efficient X-ray imaging on the subject 150.

Moreover, in connection with the interference prevention function, the system control circuitry 16 includes a control function of controlling the movement of the X-ray generator 2 and X-ray detector 3 by the holding device 8, based on the interference judgment region which is set (updated) by the setting circuitry 13.

Figure 8:
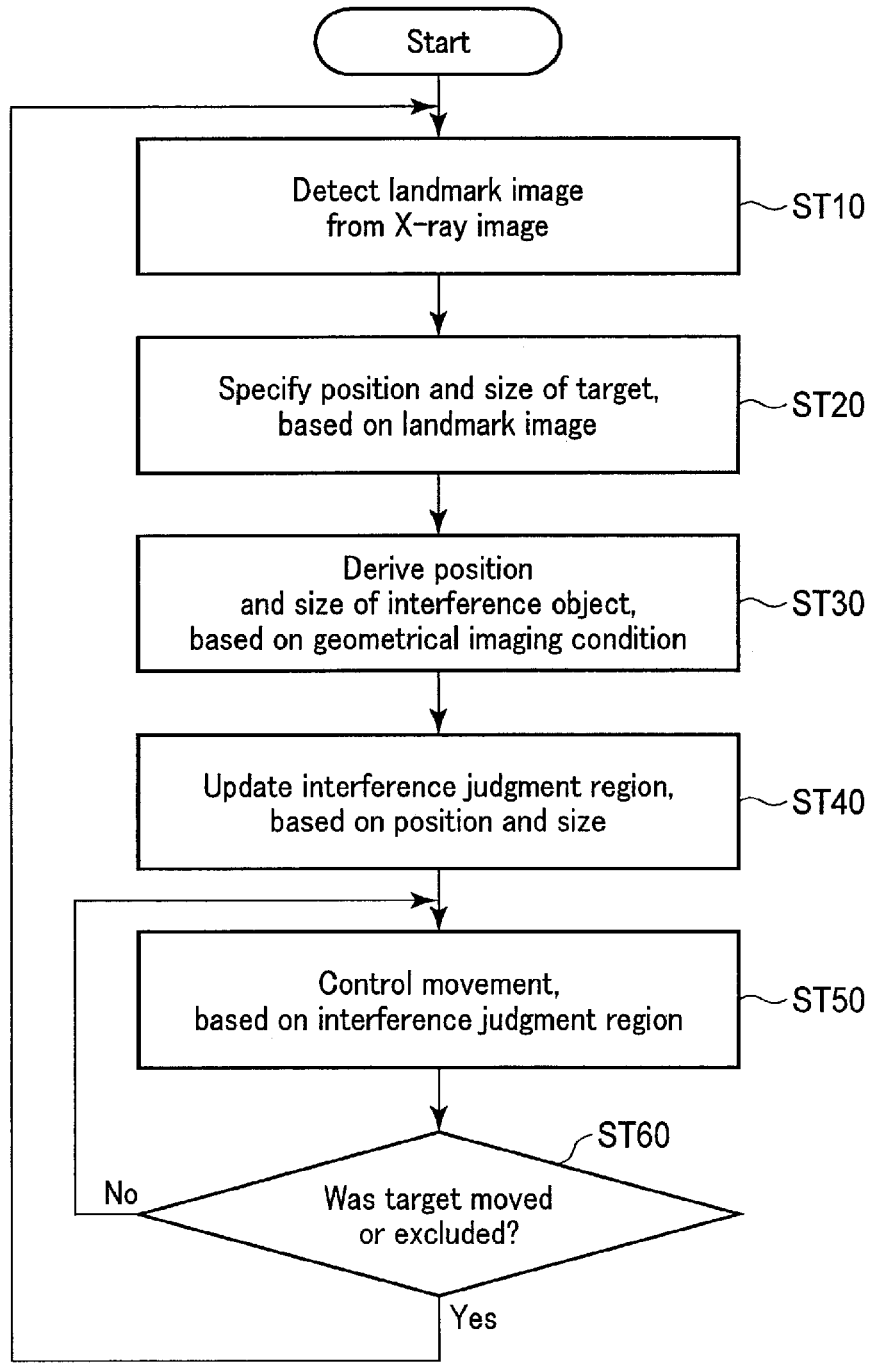
FIG. 8 is a flowchart for describing the operation in the first embodiment.
Figure 9:
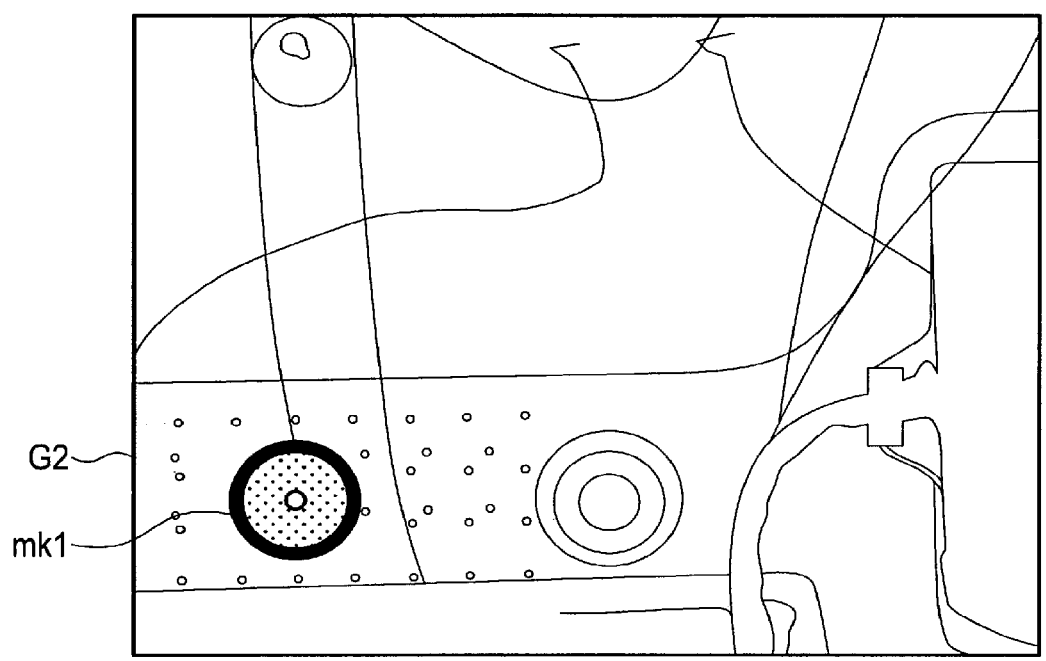
FIG. 9 is a schematic view illustrating an example of an X-ray image in the first embodiment.

Next, the operation of the X-ray diagnostic apparatus with the above-described configuration will be described with reference to a flowchart of FIG. 8 and a schematic view of FIG. 9.

Prior to X-ray imaging of the subject 150, the operator of the X-ray diagnostic apparatus 100 inputs subject information and sets X-ray emission conditions by the input interface 15. Furthermore, the operator moves/rotates the imaging system which is attached to the holding unit (C arm) 81 of the holding device 8, and the couch top 91 of the couch unit 9, on which the subject 150 is placed, to predetermined positions (initial positions).

At this time, the position information detector 11 detects the initial position information of the couch top 91, based on the driving signals which are supplied from the couch top moving mechanism driver 102 of the mechanism driving unit 10 to the horizontal moving mechanism unit and vertical moving mechanism unit of the couch unit 9 when the couch top 91 and imaging system are moved/rotated as described above. Similarly, the position information detector 11 detects the initial position information of the holding unit 81 and the imaging system attached to this holding unit 81, based on the driving signals which are supplied from the imaging system moving mechanism driver 101 to the holding unit sliding mechanism unit, holding unit holder rotating mechanism unit, stand rotating mechanism unit, floor turning arm rotating mechanism unit and imaging system sliding mechanism unit of the holding device 8.

The setting circuitry 13 sets the interference judgment region around the subject 150 placed on the couch top 91, based on the initial position information of the couch top 91 supplied from the position information detector 11, and the size information of the subject 150, the size information of the imaging system and holding unit and the size information of the couch top in the storage 12.

Next, the operator inputs a start command of X-ray fluoroscopy in the input interface 15, thereby starting X-ray fluoroscopy on the subject 150. At this time, under the observation of the fluoroscopic image data generated by the x-ray imaging unit 1 and image generation circuitry 6, the imaging system is moved toward a desired position.

On the other hand, the position information detector 11 detects the position information of the holding unit 81 and imaging system which are moving, based on the driving signals which are supplied from the imaging system moving mechanism driver 101 of the mechanism driving unit 10 to the holding unit sliding mechanism unit and holding unit holder rotating mechanism unit of the holding device 8 when the imaging system is moved, and the initial position information of the holding unit 81 and imaging system.

Here, based on the landmark in the X-ray image, the setting circuitry 13 sets (updates) the interference judgment region between the holding device and the interference object (steps ST10 to ST40). Concretely, the setting circuitry 13 executes steps ST10 to ST40 as will be described below. Specifically, as illustrated in FIG. 8, the setting circuitry 13 detects the landmark image from the X-ray image by the specifying function 13a, based on the X-ray image generated by the image generation circuitry 6 and the landmark images G1, ..., in the storage 12 (step ST10). For example, the setting circuitry 13 detects a landmark image showing the landmark mk1 illustrated in FIG. 4 from an X-ray image G2 illustrated in FIG. 9. Thereafter, based on the landmark image in the X-ray image, the setting circuitry 13 specifies the position and size of a target from the storage 12 (step ST20). In this example, the target is the location pad Lp.

Based on the specified position and size and the geometrical imaging conditions of the X-ray image, the setting circuitry 13 derives, by the deriving function 13b, the position and size of the interference object including the location pad Lp that is the target, the couch top 91 and the subject 150 (step ST30). The geometrical imaging conditions of the X-ray image include the position information and size information of the holding unit 81 and imaging system, the position information and size information of the subject model, and the position information and size information of the couch top 91.

Subsequently, based on the derived position and size, the setting circuitry 13 updates, by the update function 13c, the interference judgment region R0 between the holding device 8, which includes the X-ray generator 2 and X-ray detector 3, and the interference object (step ST40).

Thereafter, based on the updated interference judgment region R0, the system control circuitry 16 controls, via the mechanism driving unit 10, the movement of the X-ray generator 2 and X-ray detector 3 by the holding device 8 at the time of the movement/rotation of the imaging system (ST50). For example, at the time of X-ray imaging, the system control circuitry 16 constantly calculates the clearance (distance) between the imaging system and the interference object. When the imaging system enters the interference judgment region R0 in which the clearance decreases to a threshold or less, the system control circuitry 16 decelerates or stops the holding device 8 while generating an alarm sound. On the other hand, when the imaging system does not reach the interference judgment region R0, the system control circuitry 16 moves/rotates the imaging system at a normal speed. In addition, the process of step ST50 is repeatedly executed if the target having the landmark is not moved or excluded (step ST60: No). The reason for this is that when the target having the landmark is not moved or excluded, the position and size of the interference object, which were derived in step ST30, are unchanged. Besides, when the target was moved or excluded, the X-ray diagnostic apparatus returns to step ST10.

Next, under the observation of the X-ray fluoroscopic image data, the imaging system is moved/rotated at a low speed. If this imaging system is set at a desired position of the subject 150, a command signal for stopping the movement/rotation of the imaging system and a command signal for starting X-ray imaging are input in the input interface 15.

Then, the system control circuitry 16, which has received these command signals, starts the X-ray imaging on the subject 150, based on the preset X-ray imaging conditions.

As described above, according to the present embodiment, the interference judgment region between the holding device 8 and the interference object is set based on the landmark in the X-ray image. Based on the set interference judgment region, the movement of the holding device 8 is controlled. Accordingly, with respect to the interference prevention function, the clinical usefulness can be enhanced while safety is maintained.

Concretely, for example, based on the landmark image in the X-ray image, the position and size of the target are specified from the memory (storage 12). Based on the specified position and size and the geometrical imaging conditions of the X-ray image, the position and size of the interference object including the target, couch top 91 and subject 150 are derived. Based on the derived position and size, the interference judgment region R0 between the holding device 8, which includes the X-ray generator 2 and X-ray detector 3, and the interference object is updated. Based on the updated interference judgment region R0, the movement is controlled. Accordingly, with respect to the interference prevention function, the clinical usefulness can be enhanced while safety is maintained.

As a supplementary description, the present embodiment differs from the conventional art in which the interference judgment region cannot be changed while a therapy technique is being performed. Concretely, in the present embodiment, since the target is detected based on the landmark image in the X-ray image, the size of the interference object can be changed in accordance with the target, and the interference judgment region R0 corresponding to the threshold between the imaging system and the interference object can be changed. Specifically, in the present embodiment, the presence/absence of the target (e.g., optional instrument) and the position of the target can be understood by detecting the landmark of the target. In addition, since the size of the target is understood in advance, the size of the interference object can be changed in accordance with the size of the target, and the interference judgment region can be changed.

In addition, in this embodiment, a minimum necessary interference judgment region, which is optimized for an actual interference object, can be provided, although such a minimum necessary interference judgment region cannot be obtained by the conventional interference prevention function. In the conventional interference prevention function, objects other than the couch and subject cannot be recognized. Thus, from the standpoint of securing safety, a region where a moving body is decelerated or stopped is set to be wider than an actual region, based on an average model. Thus, it may appear that the moving body is uselessly decelerated or stopped, and it is possible that users, such as a doctor, have an impression that the clinical usefulness is low. By contrast, in the present embodiment, targets other than the couch and subject can be recognized. Therefore, a minimum necessary interference judgment region, which is optimized for an actual interference object, can be set.

Moreover, without adding an exclusive-use sensor, jig, etc., the interference judgment region that is optimal for a therapy technique can be updated, and thereby the efficiency of the therapy technique can be enhanced while safety is secured.

The interference judgment region in the conventional art is unchangeable and is poor in usability. By contrast, the interference judgment region of the present embodiment can constantly be changed in real time in accordance with system information (X-ray image). Thereby, this interference judgment region is changeable and is good in usability.

Second Embodiment

Next, an X-ray diagnostic device according to a second embodiment will be described with reference to FIG. 1. The same parts as in the above-described drawings are denoted by like reference numerals, and an overlapping description is omitted. Different parts will mainly be described. Similarly, in embodiments below, an overlapping description will be omitted.

The second embodiment is a modification of the first embodiment. In the configuration of the second embodiment, from the standpoint of further avoiding useless deceleration and stop, it is regarded that an interference object does not exist on a locus along which the operation was already performed, and this locus is excluded from the interference judgment region.

Concretely, the storage 12 stores, in addition to the above-described programs and information, an operation history indicating a locus along which the holding device 8 including the X-ray generator 2 and X-ray detector 3 was moved.

Accordingly, the update function 13c of the setting circuitry 13 updates, in the above-described function, the interference judgment region so as to exclude a region corresponding to this locus, based on the operation history in the storage 12.

In addition, the system control circuitry 16 may change, in the above-described function, the movement speed in the interference judgment region, based on the operation history in the storage 12.

The other configuration is the same as the configuration of the first embodiment.

Next, the X-ray diagnostic apparatus with the above-described configuration will be described with reference to a flowchart of FIG. 10 and a schematic view of FIG. 11.

Figure 10:
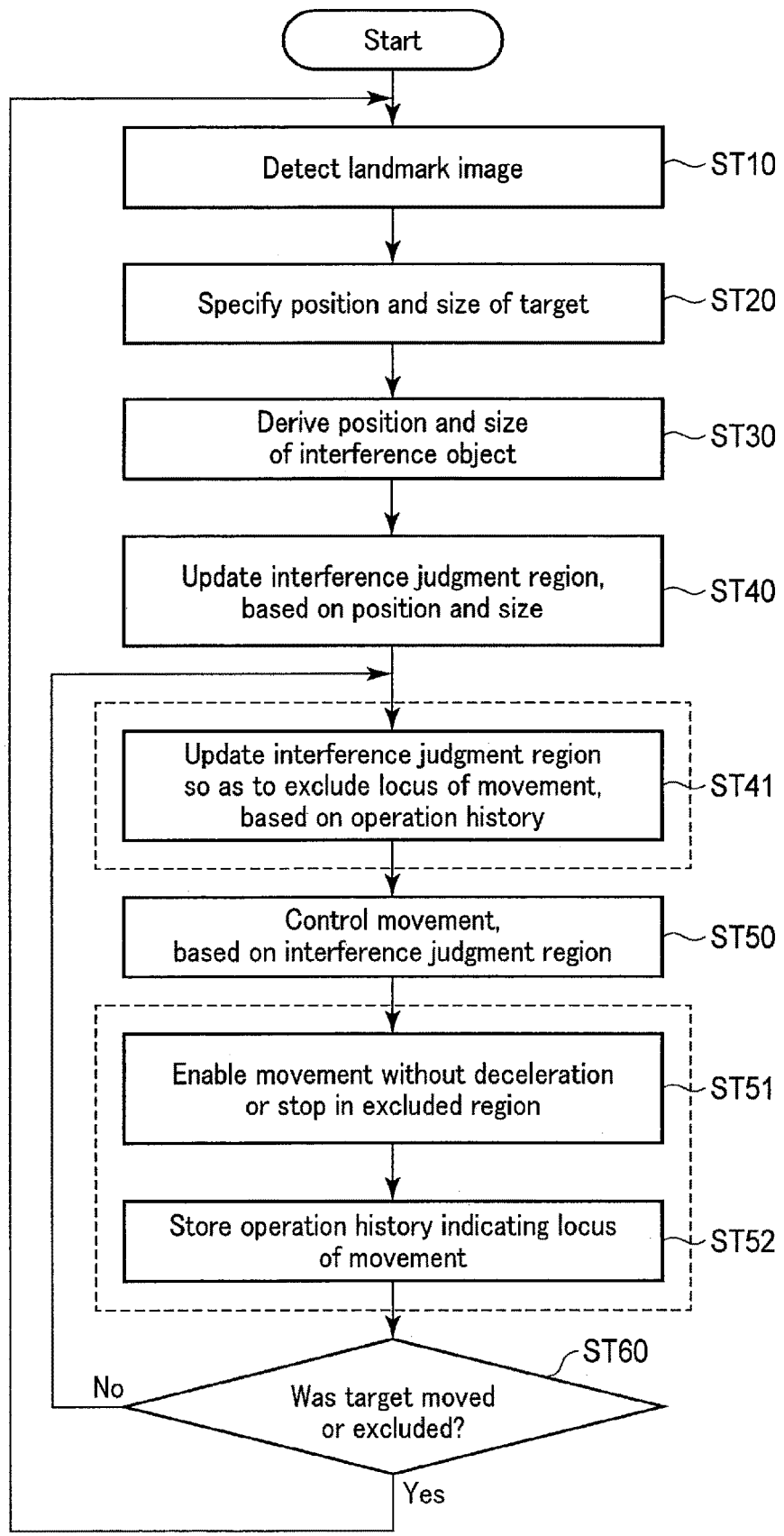
FIG. 10 is a flowchart for describing the operation of an X-ray diagnostic apparatus according to a second embodiment.

Now, as illustrated in FIG. 10, steps ST10 to ST40 are executed in the same manner as described above. However, the operation history indicating the locus of the movement of the holding device 8 is written in the storage 12. For example, the position information detector 11 executes write of the operation history.

Figure 11:
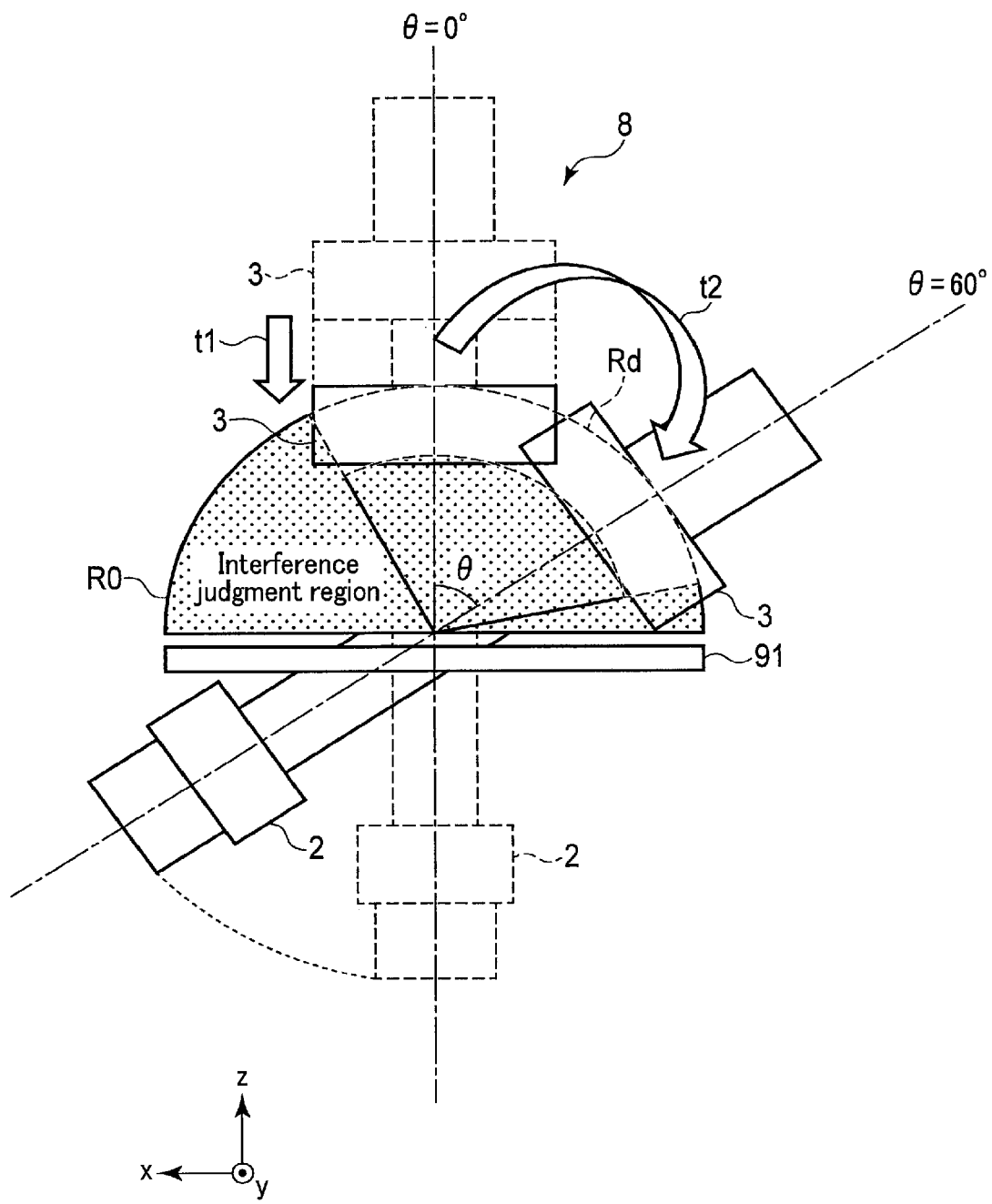
FIG. 11 is a schematic view for describing the operation in the second embodiment.

After step ST40, the setting circuitry 13 updates, by the update function 13c, the interference judgment region R0 so as to exclude (delete) a region Rd corresponding to this locus, based on the operation history in the storage 12, as illustrated in FIG. 11 (step ST41). Besides, the region Rd is excluded only in the operation in the case in which X-ray emission is started (the subject 150 is on the couch top 91) after starting an examination. The reason for this is that the subject 150 lies on the couch top 91 at the time of X-ray emission. At a time of preparation for an examination, the subject 150 is not on the couch top 91. Thus, if the region Rd is excluded at the time of preparation for an examination, it is possible that the subject 150 is, thereafter, placed in the excluded region Rd.

Based on the updated interference judgment region, the system control circuitry 16 controls the movement (ST50). At this time, the system control circuitry 16 may change the speed of movement in the interference judgement region, based on the operation history.

In any case, when the X-ray detector 3 first moves along a certain locus, the system control circuitry 16 decelerates the X-ray detector 3 (time instants t1 to t2). In addition, when the X-ray detector 3 returns in the region Rd (e.g., the same locus) excluded in step ST41, the X-ray detector 3 can move without deceleration or stop, since there is a high possibility that no interference object exists (ST51). Thus, the system control circuitry 16 moves the X-ray detector 3 without deceleration in the excluded region Rd.

Further, the operation history indicating the locus of movement of the holding device 8 is written in the storage 12, and the storage 12 stores this operation history (step ST52).

Subsequently, step ST60 is similarly executed. When the target having the landmark is not moved or excluded, steps ST41 to ST52 are repeatedly executed (step ST60: No). When the target was moved or excluded, the X-ray diagnostic apparatus returns to step ST10.

According to the present embodiment, the operation history indicating the locus of movement of the holding device 8 is stored. Based on the stored operation history, the interference judgment region is updated so as to exclude the region corresponding to this locus. Accordingly, in addition to the advantageous effects of the first embodiment, the useless deceleration or stop can be avoided when the holding device 8 passes through the same locus, and the clinical usefulness can be further enhanced.

For example, in the case of the movement between specific angles (e.g. 0°≤θ≤60°) and the movement over the same angle from a reference set position, useless deceleration or stop does not occur. Thus, quick and smooth positioning can be executed without feeling stress. Moreover, depending on therapy techniques, the situation of movement between specific angles and the movement over the same angle from a reference set position occurs frequently. Therefore, the clinical usefulness can be further enhanced.

The above advantageous effects of the second embodiment can similarly be obtained even when the movement speed is changed in the interference judgment region, based on the operation history.

Third Embodiment

Figure 12:
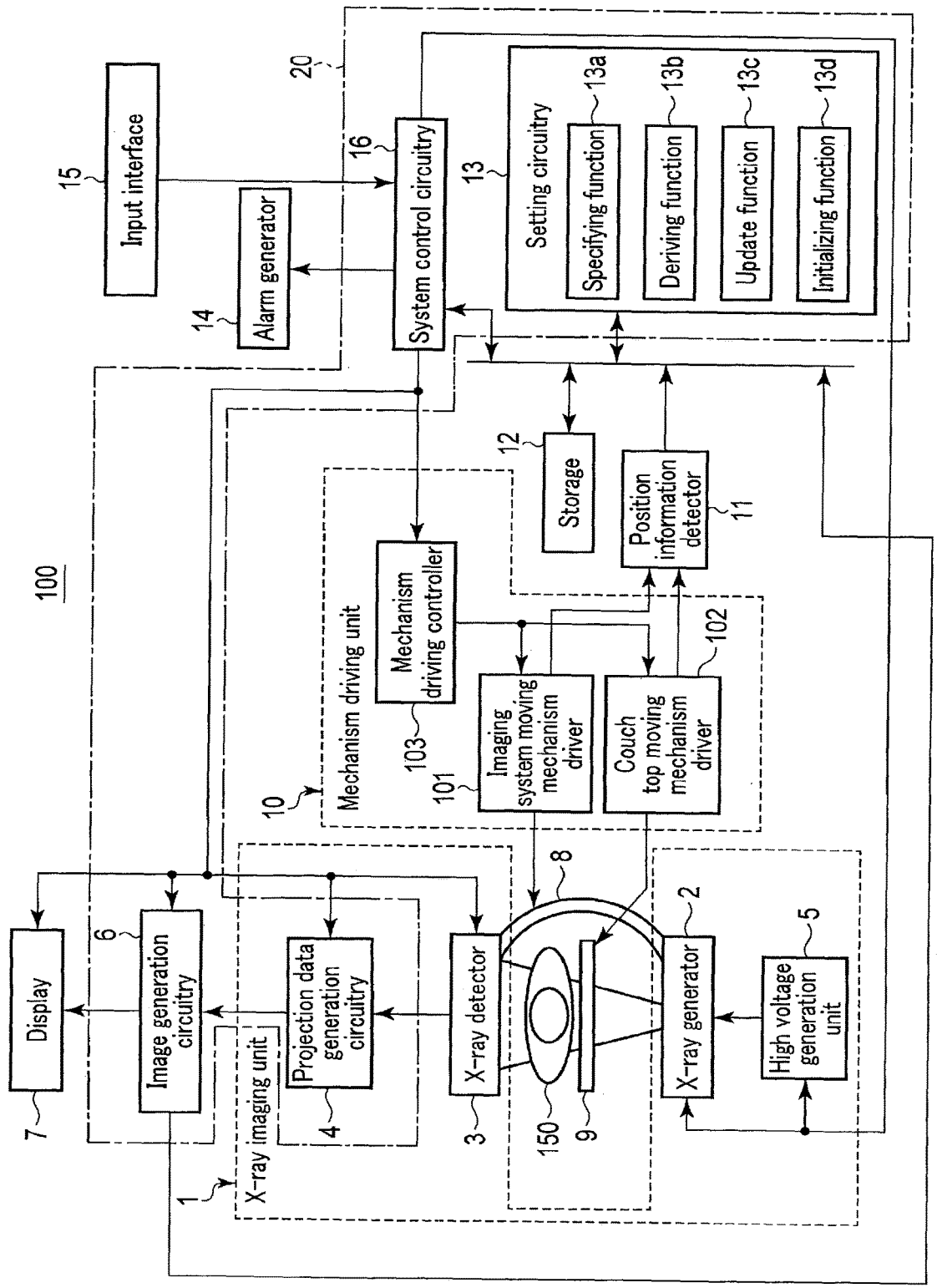
FIG. 12 is a schematic view illustrating the configuration of an X-ray diagnostic apparatus according to a third embodiment.

FIG. 12 is a schematic view illustrating the configuration of an X-ray diagnostic apparatus according to a third embodiment.

The third embodiment is a modification of the second embodiment. In the configuration of the third embodiment, from the standpoint of securing safety, the interference judgment region R0, which was decreased by excluding the region Rd, is restored to an initial value (the size prior to the exclusion of the region Rd) when a predetermined condition is satisfied.

To be more specific, in the third embodiment, when the subject 150 was moved because of the passage of time, a specific program (3D imaging, etc.) and a change of an examination, the position of the interference object has been changed. Thus, in the mode of the third embodiment, the interference judgment region R0 is restored to a default (the initial maximum judgment region).

Specifically, the setting circuitry 13 further includes an initializing function 13*d* which initializes the interference judgment region R0 so as to restore the excluded region Rd, by using as a trigger a case in which a predetermined condition is satisfied.

Here, as the predetermined condition, for example, the following can be used as needed: (a) the passage of a predetermined time, (b) a movement of the couch top 91, (c) the use of a predetermined program, (d) a movement of the X-ray detector 3 to a park position, or (e) the end of an examination. It should suffice if at least one of these five conditions is set. A discretionary combination of them can be implemented.

(a) The condition of the passage of the predetermined time is based on the fact that the passage of the predetermined time means a movement of the subject 150 in the case in which a therapy technique took a longer time than expected. For example, in EP (endoscopic papillectomy), it is possible that, due to a movement of the subject 150, the interference judgment region R0 has approached the subject 150 in a final stage. Thus, there is a possibility that it is effective to restore the interference judgment region R0 to the initial value after the passage of the predetermined time.

(b) The condition of the movement of the couch top 91 is based on the fact that to change the height of the couch top 91 means a movement of the subject 150.

(c) The condition of the use of the predetermined program is based on the fact that this use means a selection of such a kind of imaging program (3D imaging or the like) that the subject 150 or holding device 8 largely moves. The interference judgment region is restored when the initializing function 13*d* has judged that the position of the subject 150 or holding device 8 has restored to the same position as before the imaging.

(d) The condition of the movement to the park position is based on the fact that the movement to the park position means the placement of the next subject 150 when the examination was finished.

(e) The condition of the end of the examination is based on the fact that the end of the examination means the placement of the next subject 150 when the examination was finished.

The other configuration is the same as the configuration of the second embodiment.

Figure 13:
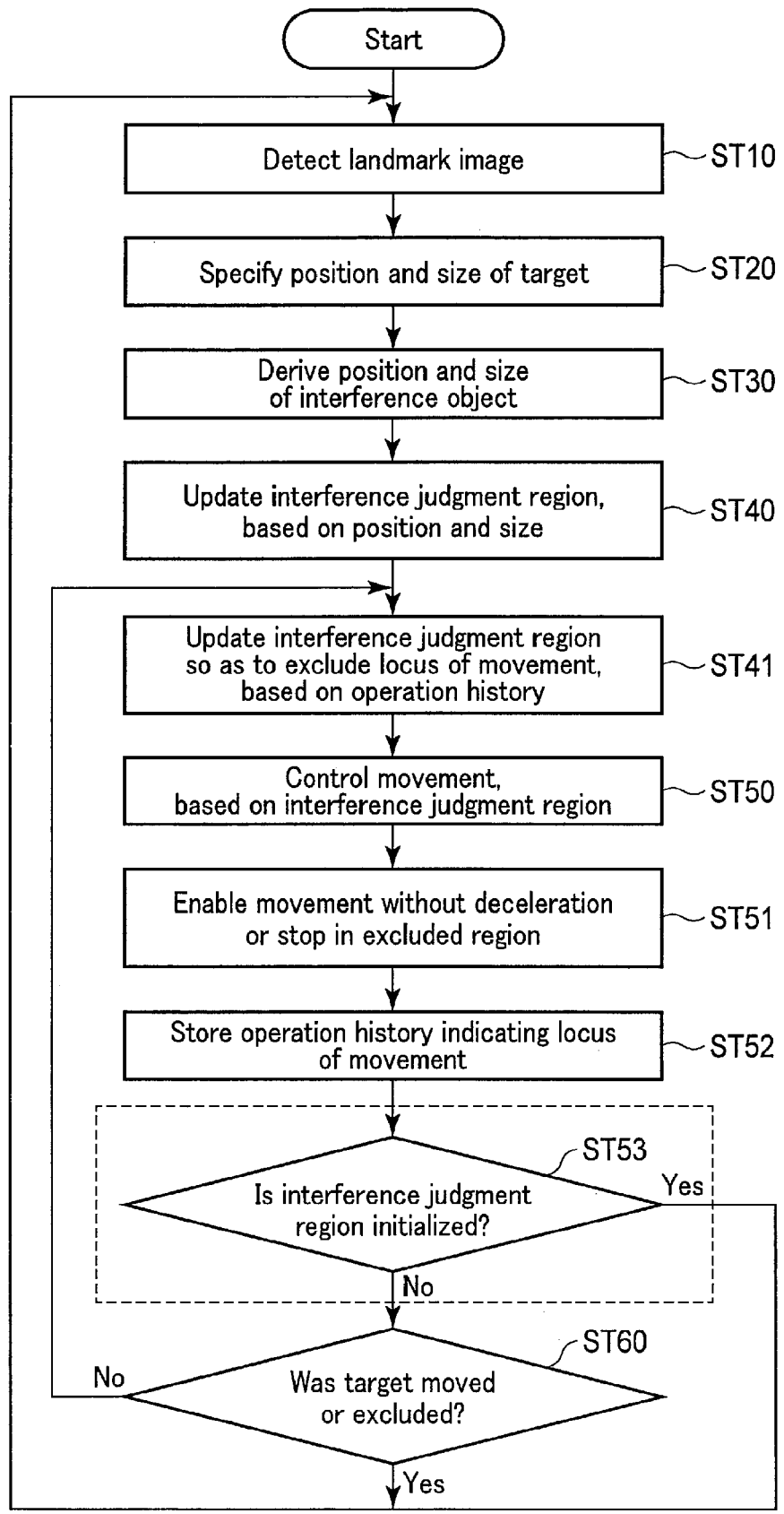
FIG. 13 is a flowchart for describing the operation in the third embodiment.

Next, the X-ray diagnostic apparatus with the above-described configuration will be described with reference to a flowchart of FIG. 13.

Now, steps ST10 to ST52 are executed in the same manner as described above.

The setting circuitry 13 determines, by the initializing function 13*d*, whether a predetermined condition is satisfied or not (step ST53). By using as a trigger the case in which the predetermined condition is satisfied, the setting circuitry 13 initializes the interference judgment region R0 so as to restore the excluded region Rd. For example, by using as a trigger the case in which a predetermined time has passed, the setting circuitry 13 returns to step ST10, thereby initializing the interference judgment region R0 (step ST53: Yes). On the other hand, when the predetermined condition is not satisfied, the setting circuitry 13 advances to step ST60.

Subsequently, step ST60 is similarly executed. When the target having the landmark is not moved or excluded, steps ST41 to ST53 are repeatedly executed (step ST60: No). In addition, in step ST60, when the target having the landmark was moved or excluded, the X-ray diagnostic apparatus returns to step ST10, and the process from step ST10 is newly executed.

According to the configuration of the present embodiment, the interference judgment region R0 is initialized so as to restore the excluded region Rd, by using as a trigger the case in which the predetermined condition is satisfied. By this configuration, in addition to the advantageous effects of the second embodiment, the safety can further be secured.

A supplementary description is given. If importance is placed on only the clinical usefulness and the deletion of the interference judgment region R0 is continued, this may result in a situation that an interference cannot be prevented. In order to prevent the occurrence of this situation, the interference judgment region R0 is initialized under a proper condition. Therefore, the safety can further be secured.

Fourth Embodiment

Next, an X-ray diagnostic apparatus according to a fourth embodiment will be described with reference to FIG. 1.

The fourth embodiment is a modification of each of the second and third embodiments. In the mode of the fourth embodiment, continuous control (e.g., fuzzy control) is executed. For example, the movement speed in the deleted region Rd is decelerated in a higher range than the movement speed in the interference judgment region. Thereby, both the clinical usefulness and the safety can be secured.

A supplementary description is given. In the second embodiment, discrete ON/OFF is executed. For example, in the deleted region Rd, the movement is executed at normal speed. In the interference judgment region, deceleration or stop is executed. In this case, the holding device 8 is very close to the interference object in such a range that the holding device 8 does not come in contact with the interference object. It is possible that the holding device 8 comes in contact with the interference object by a slight movement of the subject 150.

In the fourth embodiment, taking this possibility into account, the movement speed (or deceleration ratio) is controlled. Thereby, both the clinical usefulness and the safety can be secured.

Accordingly, the system control circuitry 16 includes, in addition to the above-described function, a function of adjusting, based on a clearance, the movement speed in the case in which the interference judgment region was deleted. Specifically, the system control circuitry 16 includes a function of controlling the movement so as to lower the movement speed in the excluded region Rd, when the interference judgment region is updated in accordance with an operation in which the clearance between the holding device 8 and the interference object becomes smaller.

For example, in a case in which a reference value is provided in the interference judgment region R0, the system control circuitry 16 includes a function of controlling the movement so as to lower the movement speed in the excluded region Rd when the clearance between the holding device 8 and the interference object is less than the reference value. Here, the reference value means a distance of a boundary which is set within the interference judgment region, and at which the risk of contact between the holding device 8 and the interference object increases.

However, the system control circuitry 16 is not necessarily limited to the case of changing the movement speed, with the reference value as the boundary. For example, when the reference value is not provided in the interference judgment region R0, the system control circuitry 16 includes a function of controlling the movement so as to continuously or intermittently lower the movement speed in the excluded region Rd at a value smaller than the movement speed on the outside of the interference judgment region R0, as the clearance between the holding device 8 and the interference object becomes smaller.

The other configuration of the fourth embodiment is the same as the configuration of the second or third embodiment.

Figure 14:
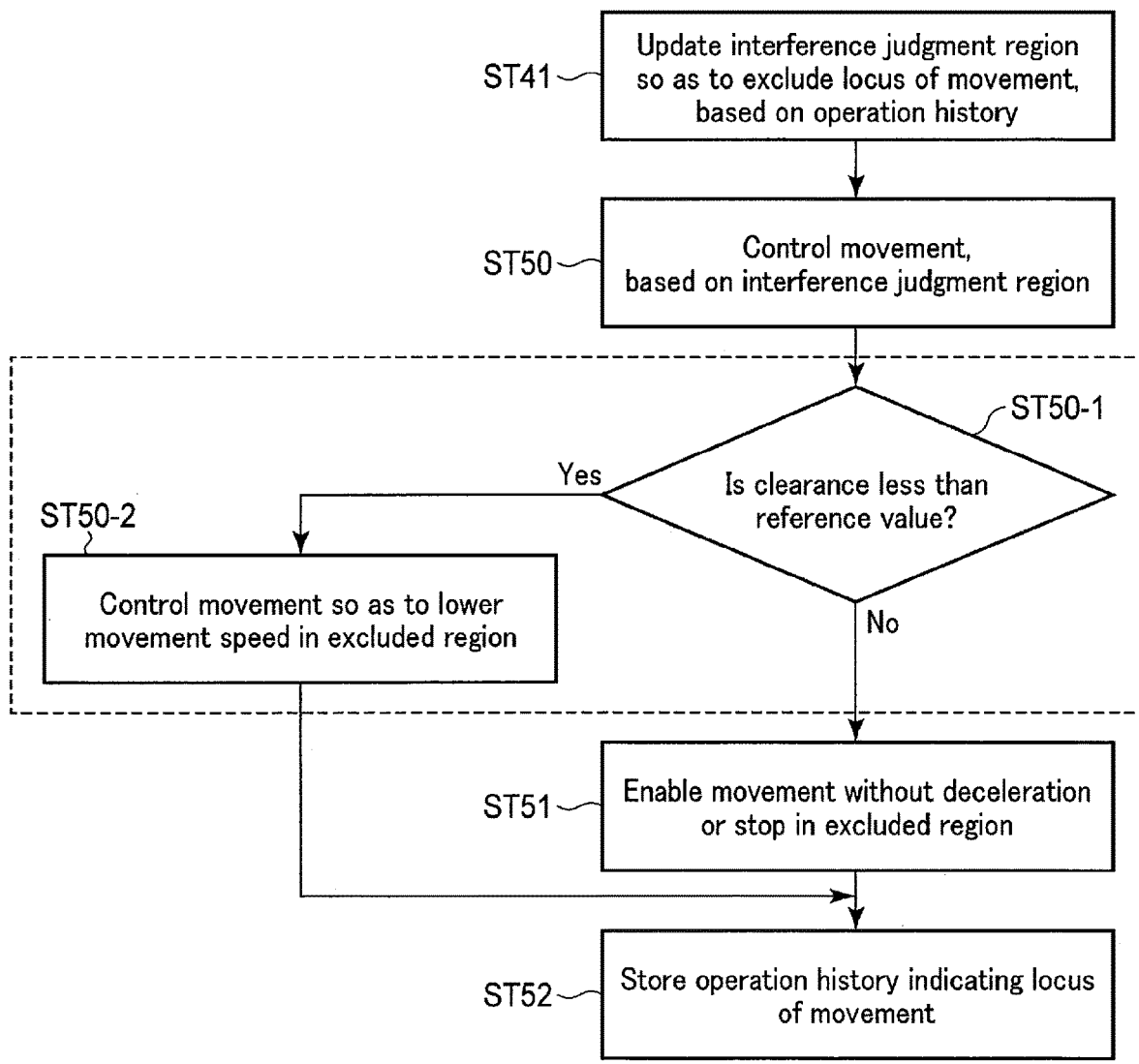
FIG. 14 is a flowchart for describing the operation of an X-ray diagnostic apparatus according to a fourth embodiment.

Next, the X-ray diagnostic apparatus with the above-described configuration will be described with reference to a flowchart of FIG. 14 and schematic views of FIG. 15, FIG. 16 and FIG. 17. Hereinafter, a description will be given of, by way of example, the case in which a reference value is set in the interference judgment region R0 with respect to the function of the system control circuitry 16.

Now, steps ST10 to ST50 are executed in the same manner as described above.

The system control circuitry 16 judges whether the clearance between the holding device 8 and the interference object is less than the reference value (step ST50-1). As a result of judgment in step ST50-1, if a clearance CL is less than the reference value, as illustrated in FIG. 15, the system control circuitry 16 controls the movement so as to lower a movement speed v2 in the excluded region Rd (step ST50-2), and goes to step ST52. Specifically, when the clearance CL is small, there is a possibility that the holding device 8 comes in contact with the interference object. It is thus necessary to make the movement speed lower than a movement speed v1 on the outside of the interference judgment region R0. On the other hand, if the movement speed is lowered to a movement speed v3 in the interference judgment region R0, the clinical usefulness lowers. Thus, in this example, as illustrated in part (a) of FIG. 16, the movement speed v2 in the excluded region Rd is set as a movement speed between the movement speeds v1 and v3. The movement speed v2 may be a fixed value. Here, the movement speeds v2 and v3 may be adjusted based on a deceleration ratio with respect to the movement speed v1 on the outside of the interference judgment region R0. For example, as shown in part (b) of FIG. 16, a deceleration ratio ηd (e.g., 25±10%) in the excluded region Rd may be made lower than a deceleration ratio η0 (50%) in the interference judgment region R0 (ηd<η0). Specifically, the respective movement speeds v2 and v3 may be adjusted as indicated in the following equations.

$$v2=(1-\eta d)\cdot v1$$

where ηd=25±10%. From this, $0.65 \cdot v1 \leq v2 \leq 0.85 \cdot v1$. The movement speed v2 may be a fixed value such as v2=0.75·v1.

$$v3=(1-\eta 0)\cdot v1$$

where η0=50%. From this, v3=0.5·v1.

It should be noted, however, that the values of ηd and η0 at a time when the clearance is small are not limited to these, and may be set at desired values within a range which satisfies the large/small relation (0<ηd<η0<1). Similarly, the values of movement speeds v1, v2 and v3 at a time when the clearance is small may be set at desired values within a range which satisfies the large/small relation (v3<v2<v1).

Besides, the movement speed v3 in the interference judgment region R0 is a speed of initial movement in the interference judgment region R0. In the case in which the clearance is small, when the holding device 8 moves along the same locus as the locus of initial movement, the holding device 8 moves at the movement speed v2.

On the other hand, when the result of judgment in step ST50-1 is "No", the process goes to step ST51. As shown in FIG. 17, when the clearance CL is the reference value or more, there is substantially no possibility that the holding device 8 comes in contact with the interference object. Thus, in step ST51, there is no need to make the movement speed lower than the movement speed v1 on the outside of the interference judgment region R0. Accordingly, in this example, when the holding device 8 first moves in the interference judgment region R0, the holding device 8 moves at the movement speed v3. When the holding device 8 moves along the same locus as the locus of the initial movement, the holding device 8 moves at the movement speed v1.

Thereafter, the process from step ST52 is executed in the same manner as described above.

According to the fourth embodiment, when the interference judgment region is updated in accordance with the operation in which the clearance (distance) between the holding device 8 and the interference object becomes smaller, the movement is controlled so as to lower the movement speed in the excluded region Rd. By this configuration, in addition to the advantageous effects of the second or third embodiment, both the clinical usefulness and the safety can be secured.

In addition, in the fourth embodiment, the description was given of, by way of example, the case in which the reference value is provided in the interference judgment region R0. Aside from this, also in the case in which the reference value is not provided in the interference judgment region R0, the same advantageous effects can be obtained.

Figure 18:
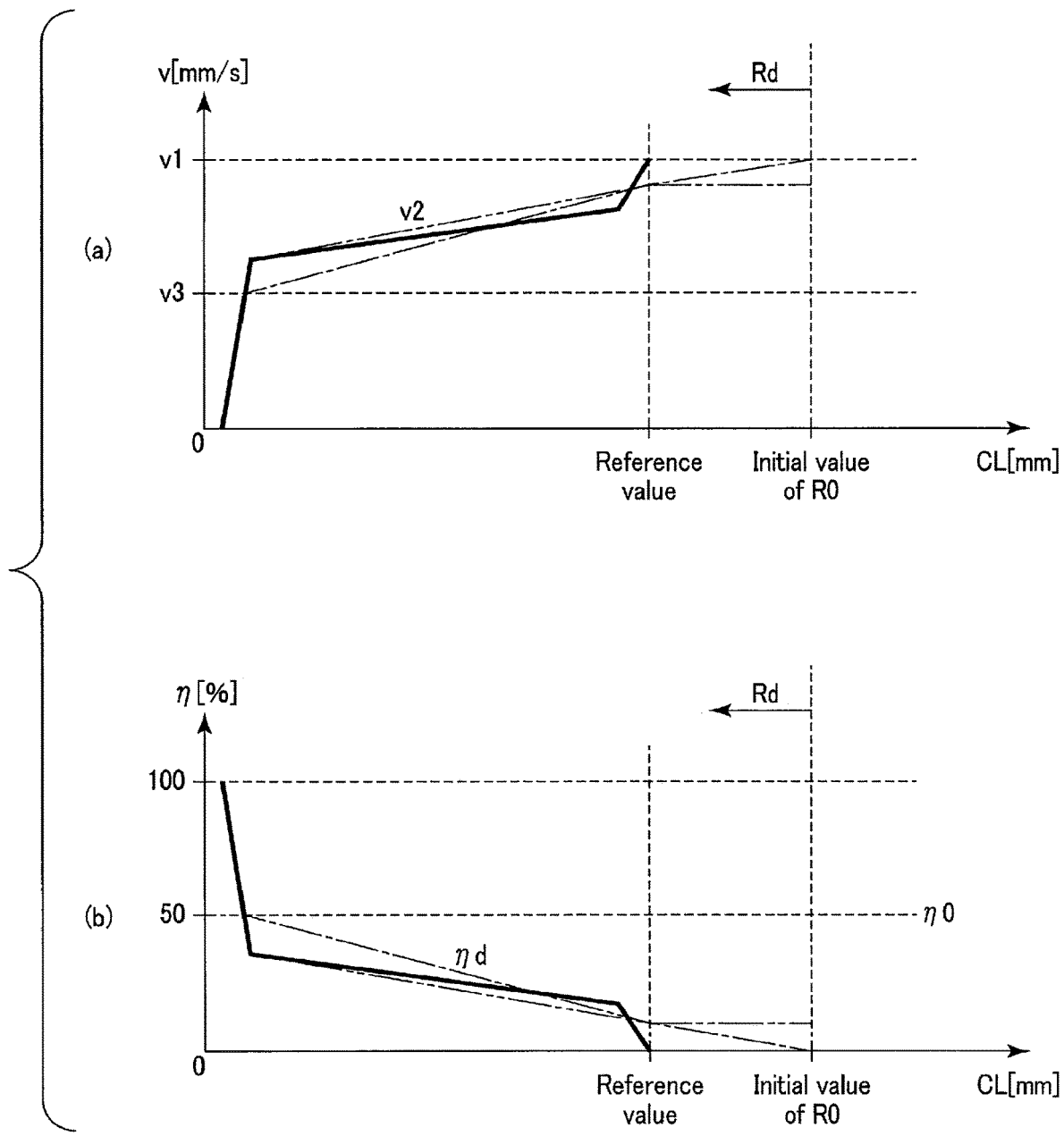
FIG. 18 is a schematic view for describing a movement speed and a deceleration ratio in a modification of the fourth embodiment.

When the reference value is not provided in the interference judgment region R0, the system control circuitry 16 controls the movement, as shown in part (a) of FIG. 18, so as to continuously or intermittently lower the movement speed v2 in the excluded region Rd at a value smaller than the movement speed v1 on the outside of the interference judgment region R0, as the clearance between the holding device 8 and the interference object becomes smaller.

In part (a) of FIG. 18, a solid line indicates the movement speed v2 in FIG. 16 for comparison.

A dot-and-dash line shows an example of the case in which the movement speed v2, which is lower than the movement speed v1, was intermittently lowered when the clearance decreased to the initial value of the interference judgment region R0 or less. Specifically, in the neighborhood of the initial value of the interference judgment region R0, the movement speed v2 is set at a fixed value. In the region apart from the initial value of the interference judgment region R0, the movement value v2 is lowered as a variable value. Besides, as the method of intermittent lowering, it is possible to use a method of stepwise lowering with no gradient portion, aside from the above-described method of lowering with a variable value (gradient portion).

A two-dot-and-dash line shows an example of the case in which the movement speed v2, which is lower than the movement speed v1, was continuously lowered when the clearance decreased to the initial value of the interference judgment region R0 or less. Here, the gradient of the movement speed v2 may be constant or may be varied like a polygonal line.

Part (b) of FIG. 18 shows deceleration ratios ηd corresponding to the movement speeds v2 indicated by the respective lines in part (a) of FIG. 18. Specifically, aside from the case of lowering the movement speed v2, the deceleration ratio ηd may be increased. For example, the system control circuitry 16 may control the movement, as shown in part (b) of FIG. 18, so as to continuously or intermittently increase the deceleration ratio ηd in the excluded region Rd at a value greater than the deceleration ratio on the outside of the interference judgment region R0, as the clearance between the holding device 8 and the interference object becomes smaller.

According to at least one of the above-described embodiments, the interference judgment region between the holding device 8 and the interference object is set based on the landmark in the X-ray image. Based on the set interference judgment region, the movement of the holding device 8 is controlled. Accordingly, with respect to the interference prevention function, the clinical usefulness can be enhanced while safety is maintained.

Besides, in each of the embodiments, the description was given of the X-ray diagnostic apparatus for a circulatory organ which includes as the holding unit 81 the floor-disposition-type C arm having end portions to which the imaging system is mounted. However, the embodiments are not restricted to this. For example, in each embodiment, the holding unit may be a ceiling-suspension-type C arm or Ω arm, and each embodiment may be a general-purpose X-ray diagnostic apparatus which is adaptive to circulatory organ diagnosis and digestive organ diagnosis.

The term "processor" used in the above description means, for example, a CPU (Central Processing Unit), a GPU (Graphics Processing Unit), or circuitry such as an ASIC (Application Specific Integrated Circuit), or a programmable logic device (e.g., SPLD (Simple Programmable Logic Device), CLPD (Complex Programmable Logic Device), FPGA (Field Programmable Gate Array)). The processor realizes functions by reading out and executing programs stored in the storage. Instead of storing programs in the storage, such a configuration may be adopted that programs are directly incorporated in the circuitry in the processor. In this case, the processor realizes functions by reading out and executing programs incorporated in the circuitry in the processor. Each of the processors in the embodiments may not be configured as single circuitry for each processor. A plurality of independent circuitries may be constructed as a single processor, and the functions of the processor may be realized. Furthermore, a plurality of structural elements in FIG. 1 may be integrated in a single processor, and the functions of the processor may be realized.

The X-ray generator 2 in each embodiment is an example of an X-ray generator in the claims. The X-ray detector 3 in each embodiment is an example of an X-ray detector in the claims. The holding device 8 in each embodiment is an example of a holding device in the claims. The storage 12 in each embodiment is an example of a memory. Processing circuitry 20 in each embodiment are examples of processing circuitry in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
a holding device including an X-ray generator configured to generate X-rays which are emitted to a subject placed on a couch top, and an X-ray detector configured to detect X-rays which have passed through the subject, the holding device being configured to movably hold the X-ray generator and the X-ray detector; and
processing circuitry configured to
generate an X-ray image of the subject, based on an output of the X-ray detector,
detect, based on the generated X-ray image and a landmark image which is stored in a memory, a landmark from the X-ray image,
set an interference judgment region between the holding device and an interference object, based on the landmark detected from the X-ray image, and
control movement of the holding device, based on the set interference judgment region.

2. The X-ray diagnostic apparatus of claim 1, wherein the landmark is a shape of a part of an instrument.

3. The X-ray diagnostic apparatus of claim 1, wherein the memory is configured to associate and store the landmark image and a position and a size of a target corresponding to the landmark image, and
wherein the processing circuitry is configured:
to detect the landmark from the generated X-ray image by referring to the stored landmark image, and to specify the position and the size of the target corresponding to the detected landmark;
to derive a position and a size of the interference object including the target, the couch top and the subject, based on the specified position and size and a geometrical imaging condition of the X-ray image; and
to set the interference judgment region between the holding device which includes the X-ray generator and the X-ray detector, and the interference object, based on the derived position and size.

4. The X-ray diagnostic apparatus of claim 1, a wherein the memory is configured to associate and store the landmark image and a position and a size of a target corresponding to the landmark image, and wherein the memory is configured to further store an operation history indicating a locus of movement of the holding device, and the processing circuitry is configured to update the interference judgment region in a manner to exclude a region corresponding to the locus, based on the operation history.

5. The X-ray diagnostic apparatus of claim 4, wherein the processing circuitry is configured to change a movement speed in the interference judgment region, based on the operation history.

6. The X-ray diagnostic apparatus of claim 4, wherein the processing circuitry configured to initialize the interference judgment in a manner to restore the excluded region, by using as a trigger a case in which a predetermined condition is satisfied.

7. The X-ray diagnostic apparatus of claim 4, wherein the processing circuitry is configured to control the movement in a manner to lower a movement speed in the excluded region, when the interference judgment region is updated in accordance with an operation in which a distance between the holding device and the interference object becomes smaller.

8. The X-ray diagnostic apparatus of claim 1, wherein the landmark image stored in a memory is an image of a magnetic pad.

9. The X-ray diagnostic apparatus of claim 1, wherein the landmark image stored in a memory is an edge of an extension auxiliary couch top.

10. The X-ray diagnostic apparatus of claim 1, wherein the landmark image stored in a memory is an edge of an arm rest.

11. The X-ray diagnostic apparatus of claim 1, wherein the landmark image stored in a memory is a head fixing instrument.

12. The X-ray diagnostic apparatus of claim 1, wherein the landmark image stored in a memory is a phantom.

13. The X-ray diagnostic apparatus of claim 1, wherein the landmark image stored in a memory is a bone of a lower limb of the subject.

14. The X-ray diagnostic apparatus of claim 1, wherein the landmark image stored in a memory is a bone of the head of the subject.

* * * * *